(12) United States Patent
Hu et al.

(10) Patent No.: US 12,421,245 B2
(45) Date of Patent: Sep. 23, 2025

(54) PHARMACEUTICALLY ACCEPTABLE ACID SALT OF FREE BASE OF GLP1 RECEPTOR AGONIST, AND PREPARATION METHOD THEREFOR

(71) Applicant: Hangzhou Zhongmei Huadong Pharmaceutical Co., Ltd., Zhejiang (CN)

(72) Inventors: Haiwen Hu, Zhejiang (CN); Li Fang, Zhejiang (CN); Fan Hu, Zhejiang (CN); Xinjie Zhou, Zhejiang (CN); Fenfen Chen, Zhejiang (CN)

(73) Assignee: Hangzhou Zhongmei Huadong Pharmaceutical Co., Ltd., Zhejiang (CN)

( * ) Notice: Subject to any disclaimer, the term of this patent is extended or adjusted under 35 U.S.C. 154(b) by 534 days.

(21) Appl. No.: 17/995,091

(22) PCT Filed: Mar. 2, 2021

(86) PCT No.: PCT/CN2021/078658
§ 371 (c)(1),
(2) Date: Sep. 29, 2022

(87) PCT Pub. No.: WO2021/196951
PCT Pub. Date: Oct. 7, 2021

(65) Prior Publication Data
US 2023/0174547 A1 Jun. 8, 2023

(30) Foreign Application Priority Data
Apr. 1, 2020 (CN) .................. 2020010248957.3

(51) Int. Cl.
*C07D 491/056* (2006.01)

(52) U.S. Cl.
CPC ...... *C07D 491/056* (2013.01); *C07B 2200/13* (2013.01)

(58) Field of Classification Search
CPC .................. C07D 491/056; C07B 2200/13
See application file for complete search history.

(56) References Cited

U.S. PATENT DOCUMENTS 4,080,472 A   3/1978   Bohuon
5,985,584 A   11/1999  Sarokin
(Continued)

FOREIGN PATENT DOCUMENTS

CN   102378574 B   11/2013
CN   104202977 A   12/2014
(Continued)

OTHER PUBLICATIONS

Ahren. GLP-1 for type 2 diabetes. Exp Cell res. 317(9): 1239-1245 (2011).
(Continued)

*Primary Examiner* — Brandon J Fetterolf
(74) *Attorney, Agent, or Firm* — WILSON SONSINI GOODRICH & ROSATI

(57) ABSTRACT

The invention provides pharmaceutically acceptable acid salts of (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl) propionic acid ("OAD2") and the preparation method thereof. The pharmaceutically acceptable acid salts of OAD2 provided herein may be useful in the treatment of various conditions and metabolic disorders including, but not limited to, type 2 diabetes.

23 Claims, 26 Drawing Sheets

(56) References Cited

U.S. PATENT DOCUMENTS

| | | |
|---|---|---|
| 6,166,042 A | 12/2000 | Ikeda et al. |
| 6,168,043 B1 | 1/2001 | Yen et al. |
| 6,172,090 B1 | 1/2001 | Ikeda et al. |
| 6,303,146 B1 | 10/2001 | Bonhomme et al. |
| 7,727,983 B2 | 6/2010 | Mjalli et al. |
| 7,790,714 B2 | 9/2010 | Mjalli et al. |
| 7,906,507 B2 | 3/2011 | Mjalli et al. |
| 8,236,345 B2 | 8/2012 | Lewis et al. |
| 8,383,644 B2 | 2/2013 | Mjalli et al. |
| 8,524,708 B2 | 9/2013 | Mjalli et al. |
| 8,703,766 B2 | 4/2014 | Mjalli et al. |
| 8,933,222 B2 | 1/2015 | Mjalli et al. |
| 8,987,295 B2 | 3/2015 | Mjalli et al. |
| 9,120,813 B2 | 9/2015 | Mjalli et al. |
| 9,175,003 B2 | 11/2015 | Mjalli et al. |
| 9,198,901 B2 | 12/2015 | Almariego et al. |
| 2011/0064806 A1 | 3/2011 | Polisetti et al. |
| 2011/0118180 A1 | 5/2011 | Silvestre et al. |
| 2011/0160198 A1 | 6/2011 | Mjalli et al. |
| 2012/0295846 A1 | 11/2012 | Hagendorf et al. |
| 2015/0313908 A1 | 11/2015 | Mjalli et al. |
| 2021/0023072 A1 | 1/2021 | Freeman et al. |
| 2023/0174546 A1 | 6/2023 | Hu et al. |

FOREIGN PATENT DOCUMENTS

| | | |
|---|---|---|
| CN | 104968341 A | 10/2015 |
| EP | 2324853 A1 | 5/2011 |
| JP | 2007314551 A | 12/2007 |
| JP | 2009507927 A | 2/2009 |
| WO | WO-0042026 A1 | 7/2000 |
| WO | WO-2005095381 A1 | 10/2005 |
| WO | WO-2007033266 A2 | 3/2007 |
| WO | WO-2007058387 A1 | 5/2007 |
| WO | WO-2009111700 A2 | 9/2009 |
| WO | WO-2010114824 A1 | 10/2010 |
| WO | WO-2011031620 A1 | 3/2011 |
| WO | WO-2011156655 A2 | 12/2011 |
| WO | WO-2012156312 A1 | 11/2012 |
| WO | WO-2013142569 A1 | 9/2013 |
| WO | WO-2014113357 A1 | 7/2014 |
| WO | WO-2019217165 A1 | 11/2019 |
| WO | WO-2021196949 A1 | 10/2021 |
| WO | WO-2021196951 A1 | 10/2021 |

OTHER PUBLICATIONS

Berge et al. Pharmaceutical Salts. Journal of Pharmaceutical Sciences 66(1):1-19 (Jan. 1977).
Davies et al. Effect of Oral Semaglutide Compared With Placebo and Subcutaneous Semaglutide on Glycemic Control in Patients With Type 2 Diabetes A Randomized Clinical Trial. 318(15):1460 (2017).
Edmonds et al. Oral GLP-1 Modulators for the Treatment of Diabetes. Annual Reports in Medicinal Chemistry 48:119-130 (2013).
Freeman et al., Abstract—TTP3859: Identification of a Non-Peptide GLP-1 Receptor Agonist That Enhances Glycemic Control in vivo, 4th G Protein-Coupled Receptors: An ASPET Colloquium, Apr. 24-25, 2013 (2013).
Freeman et al., Is Less More? Learning to Dose the Oral, Nonpeptide GLP-1R Agonist, TTP273 in Type 2 Diabetics, Poster presented at the 77th Scientific Sessions of the American Diabetes Association in San Diego. CA, Jun. 9-13, 2017.
Freeman et al., Oral Small Molecule GLP-1 Receptor (GLP-1R) Agonists for Type 2 Diabetes (T2DM) with Negligible Nausea and Vomiting, Poster presented at Keystone Conference in La Jolla, CA, Apr. 17-20, 2016.
Freeman et al., Preclinical Findings with Oral GLP-1 Receptor Agonist TTP273 Reinforce Importance of Neuro-Enteroendocrine Signaling, Poster presented at the 76th Scientific Sessions of the American Diabetes Association, Jun. 11-13, 2016.
Freeman et al., TTP273: Oral, G-protein Pathway Selective, Clinical-Stage GLP-1 Receptor (GLP-1R) Agonist, Poster presented at G Protein-Coupled Receptors: Structure, Signaling and Drug Discovery, Keystone Symposia on Molecular and Cellular Biology, Keystone, Colorado, Feb. 22, 2016.
Freeman et al., TTP273. Oral (Nonpeptide) GLP-1R Agonist• Improved Glycemic Control without Nausea and Vomiting in Phase 2, Poster presented at the 77th Scientific Sessions of the American Diabetes Association in San Diego, CA, Jun. 9-13, 2017.
Freeman et al., TTP3859: Identification of a Non-Peptide GLP-1 Receptor Agonist That Enhances Glycemic Control in vivo, 4th G Protein-Coupled Receptors: An ASPET Colloquium, Apr. 24-25, 2013.
Gustavson et al., Abstract—TTP054. a Novel, Orally-Available Glucagon-Like Peptide-1 (GLP-1) Agonist, Lowers HbA1 c in Subjects with Type 2 Diabetes Mellitus (T2DM). Jun. 2014. ADA 74th Scientific Sessions (156-OR).
Gustavson et al., Abstract—TTP273, an Orally-Available Glucagon-Like Peptide-1 (GLP-1) Agonist, Notably Reduces Glycemia in Subjects with Type 2 Diabetes Mellitus (T2DM). Jun. 2014. ADA 74th Scientific Sessions. (155-OR).
Gustavson et al., TTP054, a Novel, Orally-Available Glucagon-Like Peptide-1 (GLP-1) Agonist, Lowers HbA1c in Subjects with Type 2 Diabetes Mellitus (T2DM). Jun. 2014. ADA 74th Scientific Sessions. (156-OR).
Gustavson et al. TTP054, a Novel, Orally-Available Glucagon-like Peptide-1 (GLP-1) Agonist, Lowers HbA1c in Subjects with Type 2 Diabetes Mellitus (T2DM). Diabetes 63(Suppl. 1):A41-A42 (Jun. 2014).
Gustavson et al., TTP273, an Orally-Available Glucagon-Like Peptide-1 (GLP-1) Agonist, Notably Reduces Glycemia in Subjects with Type 2 Diabetes I Mellitus (T2DM). Jun. 2014. ADA 74th Scientific Sessions. (155-OR).
Nauck et al., Efficacy and safety comparison of liraglutide, glimepiride, and placebo, all in combination with metformin, in type 2 diabetes: the LEAD (liraglutide effect and action in diabetes)-2 study. Diabetes Care 32(1):84-90 (2009).
PCT/CN2021/078622 International Search Report and Written Opinion dated May 26, 2021.
PCT/CN2021/078658 International Search Report and Written Opinion dated May 21, 2021.
Sivertsen et al. The effect of glucagon-like peptide 1 on cardiovascular risk. Nature Reviews Cardiology 9(4):209-222 (2012).
Su et al., Boc5, a non-peptidic glucagon-like Peptide-1 receptor agonist, invokes sustained glycemic control and weight loss in diabetic mice. PLOS One 3(8): e2892 (2008).
Wootten et al., Differential Activation and Modulation of the Glucagon-Like Peptide-1 Receptor by Small Molecule Ligands. Mol Pharmacol 83:822-834 (2013).
Zhao et al. Activation of the GLP-1 receptor by a non-peptidic agonist. Nature 577(7790):432-436 (2020).
Anderson, Bradley D et al. Chapter 34: Preparation of water-soluble organic compounds by salt formation. Latest Drug Discovery Chemistry 2:347-365 (1999).
Chapter 4: Pharmaceutical crystallization method. Preparation of organic compound crystal—Principle and know-how:57-79 (2008). General Test methods. Sixteenth Revised Japanese Pharmacopoeia:64-68 (2011).
Caira. Crystalline Polymorphism of Organic Compounds. Topics in Current Chemistry. 198:163-208 (Jan. 1998).
Stahl, Heinrich P, et al., Usage frequency of acids and bases for forming drug salts. Handbook of Pharmaceutical Salts. Verlag Helvetica Chimica Acta, Zurich (pp. 329-350) (2002).

PHARMACEUTICALLY ACCEPTABLE ACID SALT OF FREE BASE OF GLP1 RECEPTOR AGONIST, AND PREPARATION METHOD THEREFOR

TECHNICAL FIELD

The invention belongs to the technical field of medicine, and particularly relates to pharmaceutically acceptable acid salts of (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl)propionic acid ("OAD2"), and the preparation methods thereof. The pharmaceutically acceptable acid salts of the invention may be useful in the treatment of various conditions and metabolic disorders including, but not limited to, type 2 diabetes.

BACKGROUND OF THE INVENTION (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl)propionic acid dihydrochloride (referred to herein as OAD2 dihydrochloride), is an orally available, non-peptide glucagon-like peptide 1 receptor (GLP-1R) agonist. It has an empirical formula of $C_{50}H_{49}Cl_4N_3O_6$, a molecular weight of 929.76, and the following chemical structure:

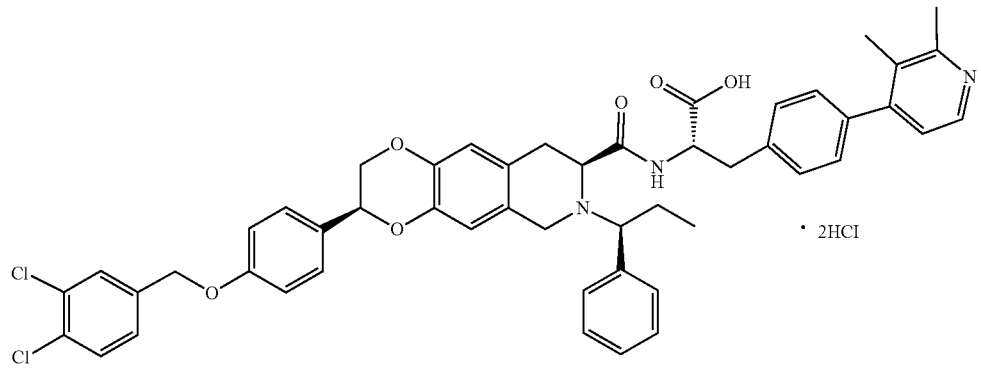

OAD2 dihydrochloride

In addition to a patent for invention CN102378574B disclosing OAD2 dihydrochloride and the free base thereof, other acid salts of OAD2 or the crystal forms thereof have not been systematically studied. Therefore, it is desirable to further screen pharmaceutically acceptable acid salts of OAD2 and the crystal forms thereof.

SUMMARY OF THE INVENTION

The objective of the invention is to provide pharmaceutically acceptable acid salts of OAD2: (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl) propionic acid, and the preparation methods thereof.

To solve the above technical problems, the invention provides the following technical solutions:

The invention provides pharmaceutically acceptable acid salts of OAD2. In certain embodiments, the pharmaceutically acceptable acid salts of OAD2 may be crystalline. In another embodiment, the pharmaceutically acceptable salt of OAD2 is anhydrous, a hydrate, or a solvate. The invention also provides a method of making pharmaceutically acceptable acid salts of OAD2.

According to the invention, the crystalline acid salts of OAD2 include: crystal form B of hydrochloride, crystal form C of hydrochloride, crystal form C of p-toluenesulfonate, crystal form C of tartrate, crystal form C of citrate, crystal form C of glycollate, crystal form C of methanesulfonate, crystal form C of hydrobromide, crystal form D of hydrobromide, and crystal form C of sulfate.

The invention further provides a pharmaceutical composition comprising one or more pharmaceutically acceptable acid salt forms of OAD2. The invention also provides methods of producing a pharmaceutical composition comprising one or more pharmaceutically acceptable acid salt forms of OAD2.

The invention also provides use of a pharmaceutically acceptable acid salt of OAD2 for the preparation of a GLP-1 receptor agonist.

The invention also provides use of a pharmaceutically acceptable acid salt of OAD2 for the preparation of a medicament. In an embodiment, the medicament may be for treating diabetes.

The invention also provides methods of treatment comprising administering to a human in need thereof a therapeutically effective amount of a pharmaceutically acceptable acid salt of OAD2. The methods of treatment may be useful to treat a disorder or condition where activation of the GLP-1 receptor is beneficial.

These and other embodiments of the invention are described in greater detail in the detailed description of the invention which follows.

The pharmaceutically acceptable acid salts of OAD2 may achieve the following beneficial effects. Compared with OAD2 dihydrochloride, the pharmaceutically acceptable acid salts of OAD2 disclosed herein may have improved hygroscopicity. For example, but not limited to, crystal form B of hydrochloride, crystal form C of p-toluenesulfonate and crystal form C of sulfate show superior stability relative to OAD2 dihydrochloride.

DETAILED DESCRIPTION OF THE INVENTION

Figure 1:
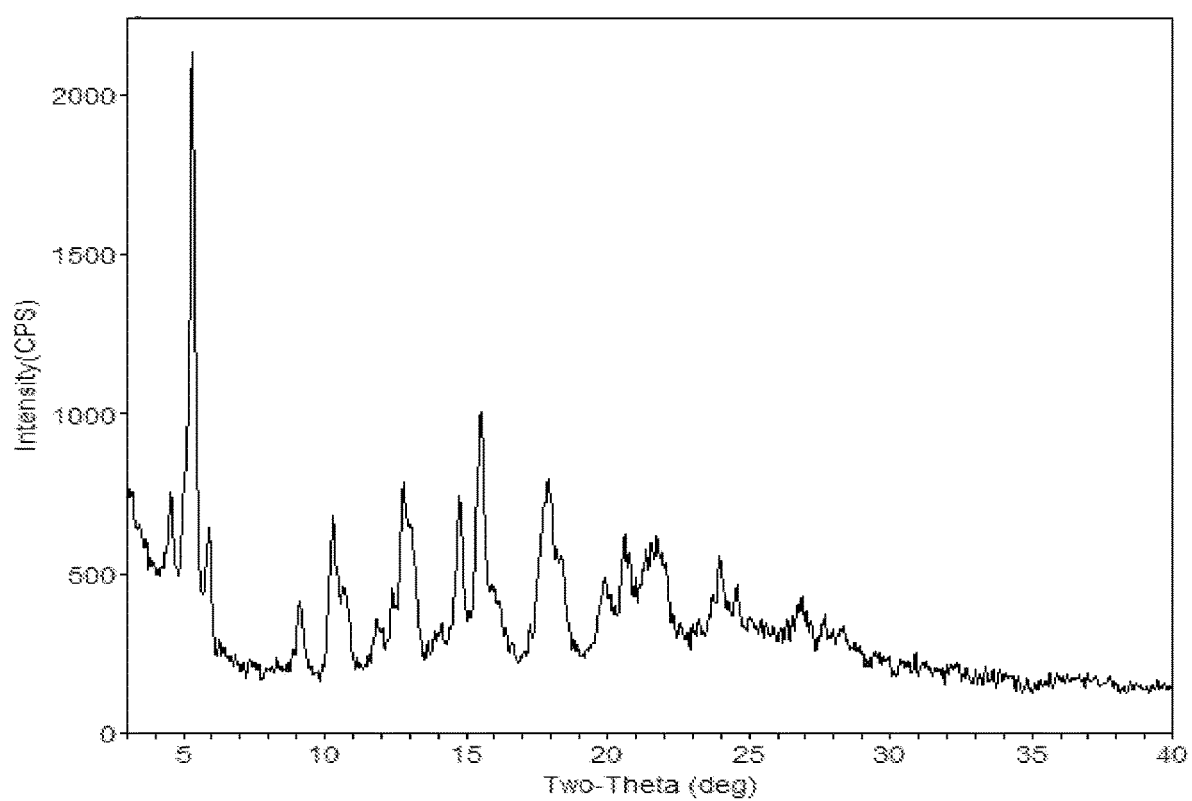
FIG. 1 shows the XRPD of crystal form B of hydrochloride.

The invention will be further illustrated by combining the following specific examples. The following examples are used to explain the method of the invention and the core concept thereof, and for those skilled in the art, any possible change or substitution without departing from the inventive concept will fall within the protection scope of the invention. In the following examples, where the specific conditions of the experimental methods are not indicated, they are typically the conventional conditions, or are those recommended by the raw material or commodity manufactures; and the solvents without indicating the source are typically conventional solvents that are commercially available.

In the invention, "crystals" or "crystal form" is identified by the characterization of the indicated X-ray powder diffraction pattern. Those skilled in the art will appreciate that the experimental error of the characterization data typically depends on the conditions of the instrument, the preparation and purity of the sample, etc. Particularly, it is well known to those skilled in the art that X-ray powder diffraction pattern usually changes with the variation of experimental conditions, and accordingly the peak intensity per se cannot be identified as the only or decisive factor. The experimental error of peak angle is usually within 5% or less, and the data of peak angle usually allows for an error of ±0.2. In addition, owning to the influence of experimental factors such as the height of the sample, the peak angles may shift as a whole, and thus a certain shift is usually allowed. Those skilled in the art will appreciate that any crystal form having characteristic peaks same as or similar to those as shown in the X-ray powder diffraction pattern of the invention will fall within the protection scope of the invention. The value of the melting point as illustrated in the DSC thermogram should be interpreted as a value within a range of that numerical±3.0° C., and preferably within a range of that numerical±1.0° C.

The term "therapeutically effective amount" is used herein to denote the amount of the pharmaceutically acceptable acid salt of OAD2 that will elicit the therapeutic response of a subject that is being sought. In an embodiment, the therapeutic response may be agonizing the GLP-1 receptor.

OAD2 as a free base may be obtained according to the method as described in patent CN102378574B or in the related international publication WO 2010/114824, which are incorporated herein by reference in their entirety.

Pharmaceutically Acceptable Salts of OAD2

The invention provides pharmaceutically acceptable acid salts of (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl)propionic acid ("OAD2").

In one embodiment, the present invention is a pharmaceutically acceptable acid salt formed between OAD2 and a pharmaceutically acceptable acid. In one embodiment, the pharmaceutically acceptable acid is selected from the group consisting of 1-hydroxy-2-naphthoic acid, 4-aminosalicylic acid, adipic acid, L-aspartic acid, benzene sulfonic acid, benzoic acid, trans-cinnamic acid, citric acid, fumaric acid, galactaric acid, gentisic acid, gluconic acid, glutamic acid, glutaric acid, glycolic acid, hexanoic acid, hippuric acid, hydrobromic acid, hydrochloric acid, L-lactic acid, maleic acid, L-malic acid, malonic acid, R-mandelic acid, methane sulfonic acid, naphthalene sulfonic acid, nicotinic acid, oxalic acid, palmitic acid, phosphoric acid, propionic acid, saccharin, salicyclic acid, stearic acid, succinic acid, sulfuric acid, L-tartaric acid, p-toluenesulfonic acid, vanillic acid, and vanillin. In one embodiment, the pharmaceutically acceptable acid is selected from the group consisting of hydrobromic acid, hydrochloric acid, p-toluenesulfonic acid, tartaric acid, citric acid, glycolic acid, methanesulfonic acid, and sulfonic acid.

In certain embodiments, the pharmaceutically acceptable acid salts of OAD2 may be crystalline. In another embodiment, the pharmaceutically acceptable acid salt of OAD2 is anhydrous, a hydrate, or a solvate.

According to the invention, the crystalline acid salts of OAD2 include: crystal form B of hydrochloride, crystal form C of hydrochloride, crystal form C of p-toluenesulfonate, crystal form C of tartrate, crystal form C of citrate, crystal form C of glycollate, crystal form C of methanesulfonate, crystal form C of hydrobromide, crystal form D of hydrobromide, and crystal form C of sulfate.

As a specific embodiment, in the above crystalline acid salts of OAD2, the salt formation ratio (molar ratio) is in the range of acid:free base=0.3:1~1:1, but is not limited to that range, as the salt formation ratio (molar ratio) is in connection with the amount of the acid.

Hydrochloride

As a specific embodiment, the invention provides a crystal form B of hydrochloride of OAD2, which has an X-ray powder diffraction pattern comprising peaks at the following diffraction angles (2θ): 5.3±0.2°, 9.2±0.2°, 10.3±0.2°, 13.2±0.2°, and 14.8±0.2°; and preferably, the X-ray powder diffraction pattern comprises substantially the same peaks at the 2θ diffraction angles as shown in FIG. 1, and the X-ray powder diffraction data is as shown in Table 1.

Figure 11:
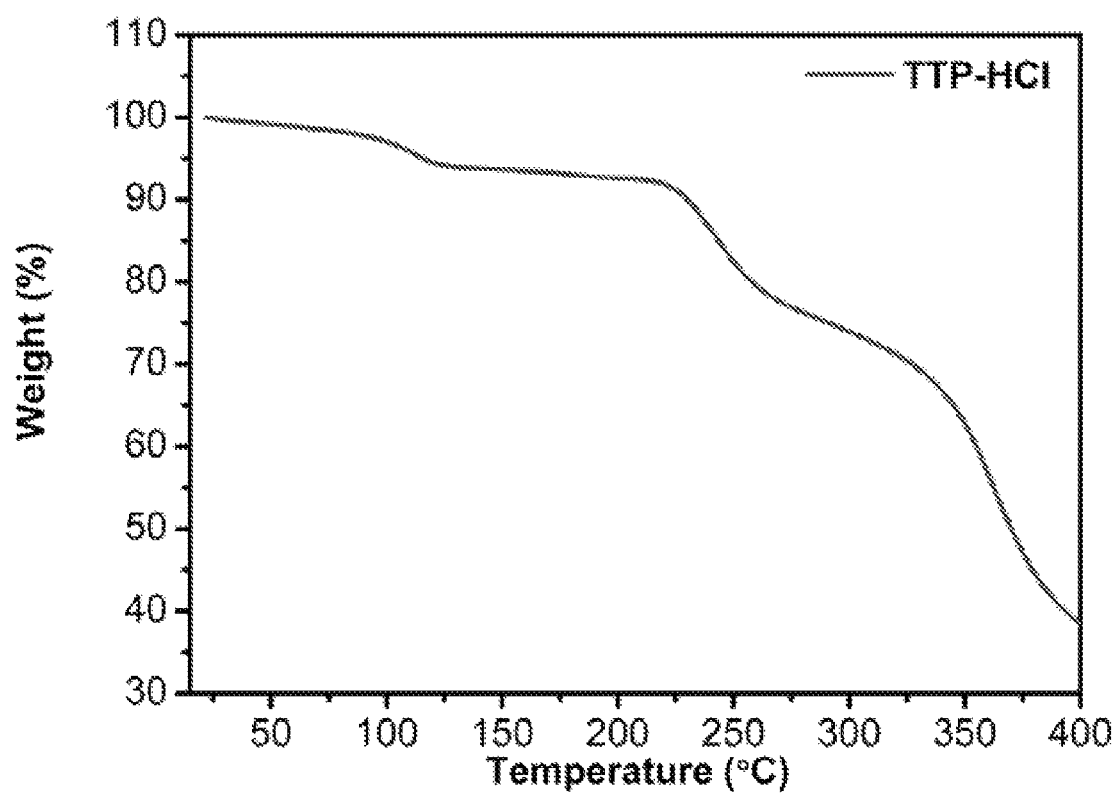
FIG. 11 shows the TGA thermogram of crystal form B of hydrochloride.
Figure 12:
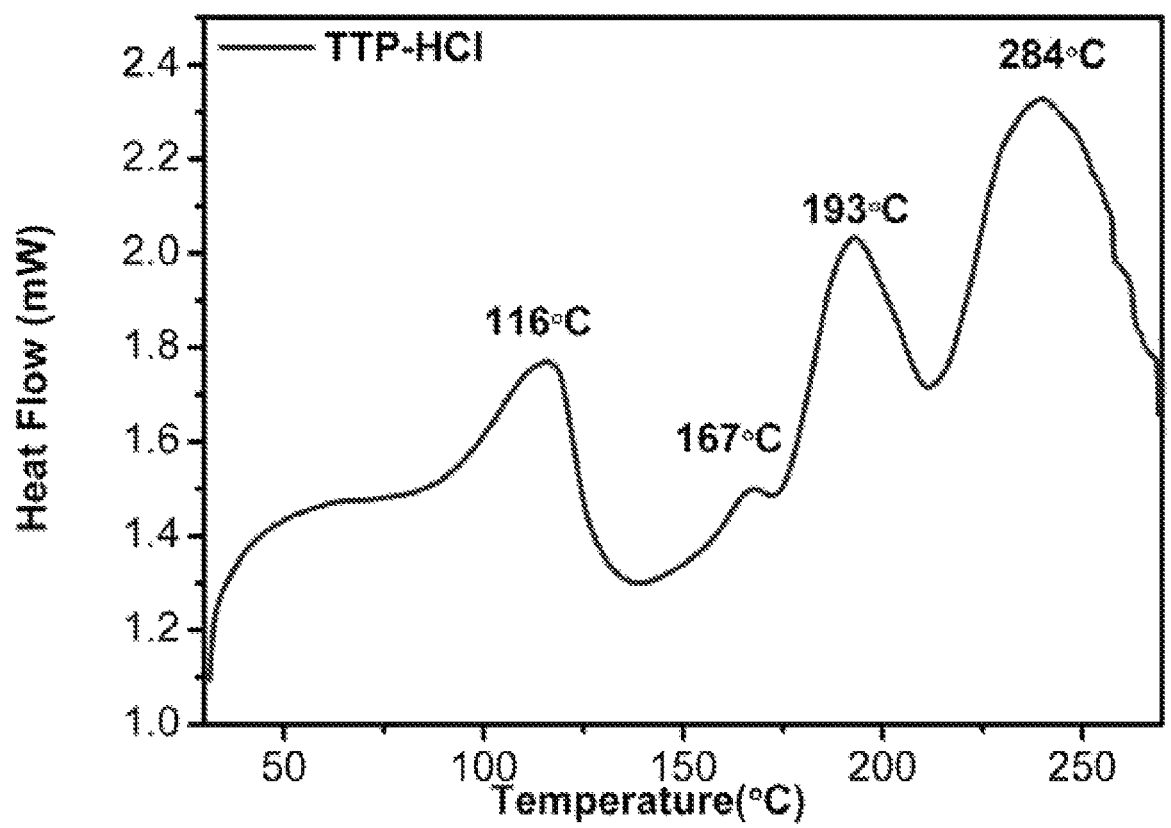
FIG. 12 shows the DSC thermogram of crystal form B of hydrochloride.

In another embodiment, the crystal form B of hydrochloride of OAD2 is characterized by an $^1$H NMR spectrum. In another embodiment, the crystal form B of hydrochloride of OAD2 is characterized by an endothermic peak at 116° C. and/or 193° C. as determined by DSC. In another embodiment, the crystal form B of hydrochloride of OAD2 is characterized by a DSC profile as showing in FIG. 12. In another embodiment, the crystal form B of hydrochloride of OAD2 is characterized by a TGA profile as shown in FIG. 11. In another embodiment, the crystal form B of hydrochloride of OAD2 is characterized by at least two of the following features:
  i) an XRPD pattern comprising peaks at the following diffraction angles (2θ): 5.3±0.2°, 9.2±0.2°, 10.3±0.2°, 13.2±0.2°, and 14.8±0.2°;
  ii) a DSC profile as shown in FIG. 12; or
  iii) a TGA profile as shown in FIG. 11.

Figure 2:
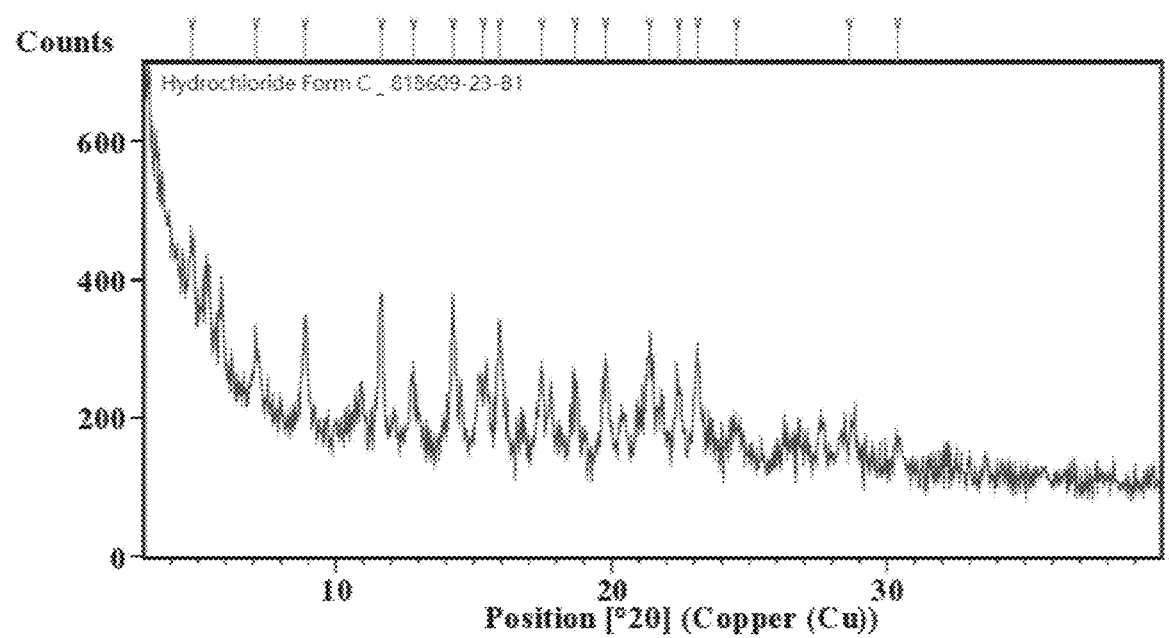
FIG. 2 shows the XRPD of crystal form C of hydrochloride.

As a specific embodiment, the invention provides a crystal form C of hydrochloride of OAD2, which has an X-ray powder diffraction pattern comprising peaks at the following diffraction angles (2θ): 8.9±0.2°, 11.6±0.2°, 14.3±0.2°, 15.9±0.2°, 21.4±0.2°, and 23.1±0.2°; and preferably, the X-ray powder diffraction pattern comprises substantially the same peaks at the 2θ diffraction angles as shown in FIG. 2, and the X-ray powder diffraction data is as shown in Table 1.

Figure 13:
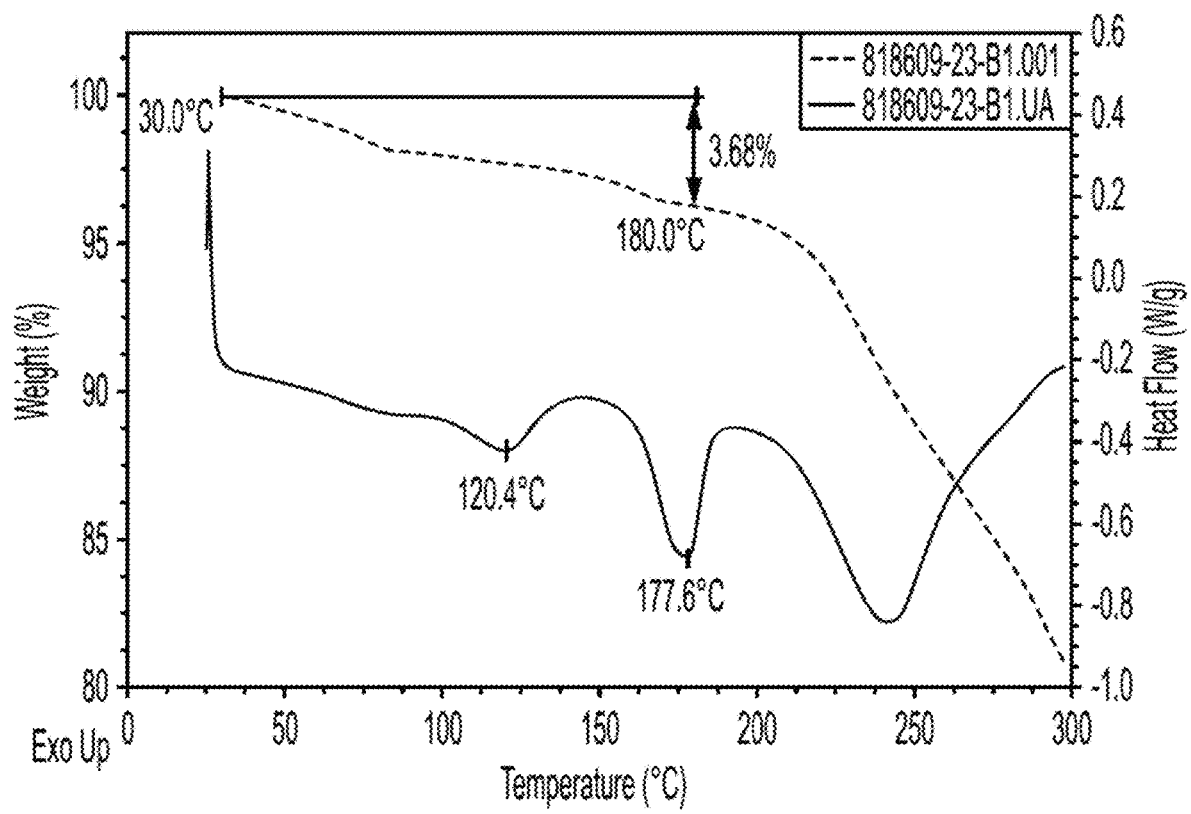
FIG. 13 shows the TGA/DSC thermograms of crystal form C of hydrochloride.

In another embodiment, the crystal form C of hydrochloride of OAD2 is characterized by an $^1$H NMR spectrum. In another embodiment, the crystal form C of hydrochloride of OAD2 is characterized by an endothermic peak at 120.4° C. and/or 177.6° C. as determined by DSC. In another embodiment, the crystal form C of hydrochloride of OAD2 is characterized by a DSC profile as showing in FIG. 13. In another embodiment, the crystal form C of hydrochloride of OAD2 is characterized by a TGA profile as shown in FIG. 13. In another embodiment, the crystal form C of hydrochloride of OAD2 is characterized by at least two of the following features:
  i) an XRPD pattern comprising peaks at the following diffraction angles (2θ): 8.9±0.2°, 11.6±0.2°, 14.3±0.2°, 15.9±0.2°, 21.4±0.2°, and 23.1±0.2°;
  ii) a DSC profile as shown in FIG. 13; or
  iii) a TGA profile as shown in FIG. 13.

P-Toluenesulfonate

Figure 3:
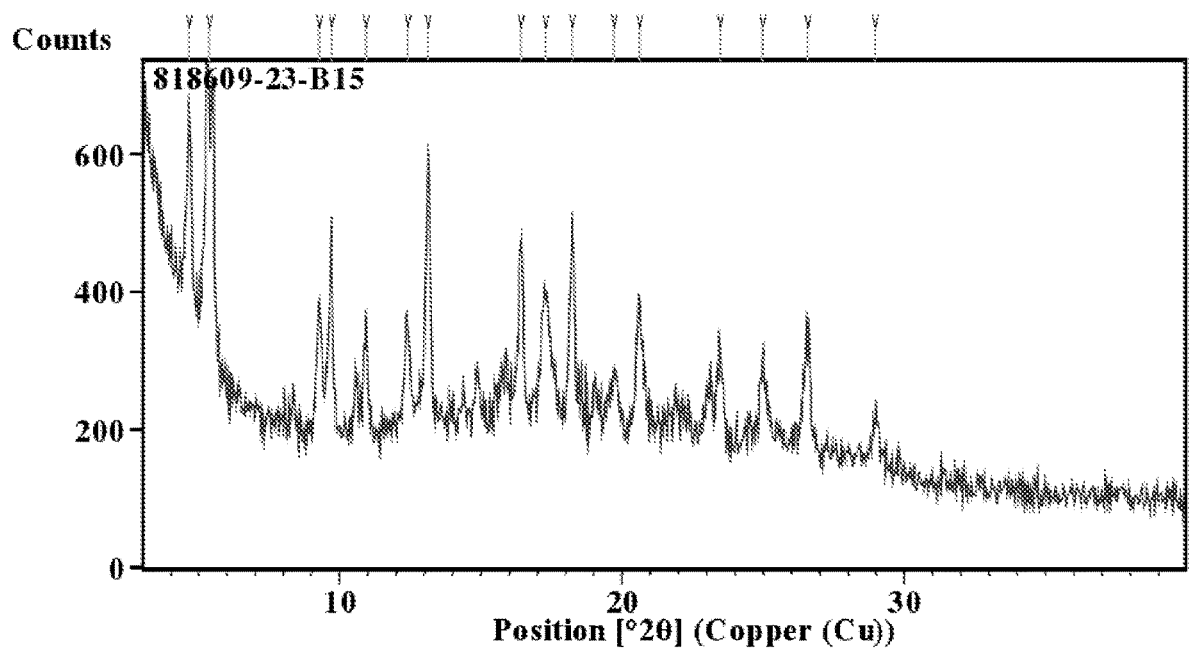
FIG. 3 shows the XRPD of crystal form C of p-toluenesulfonate.
Figure 14:
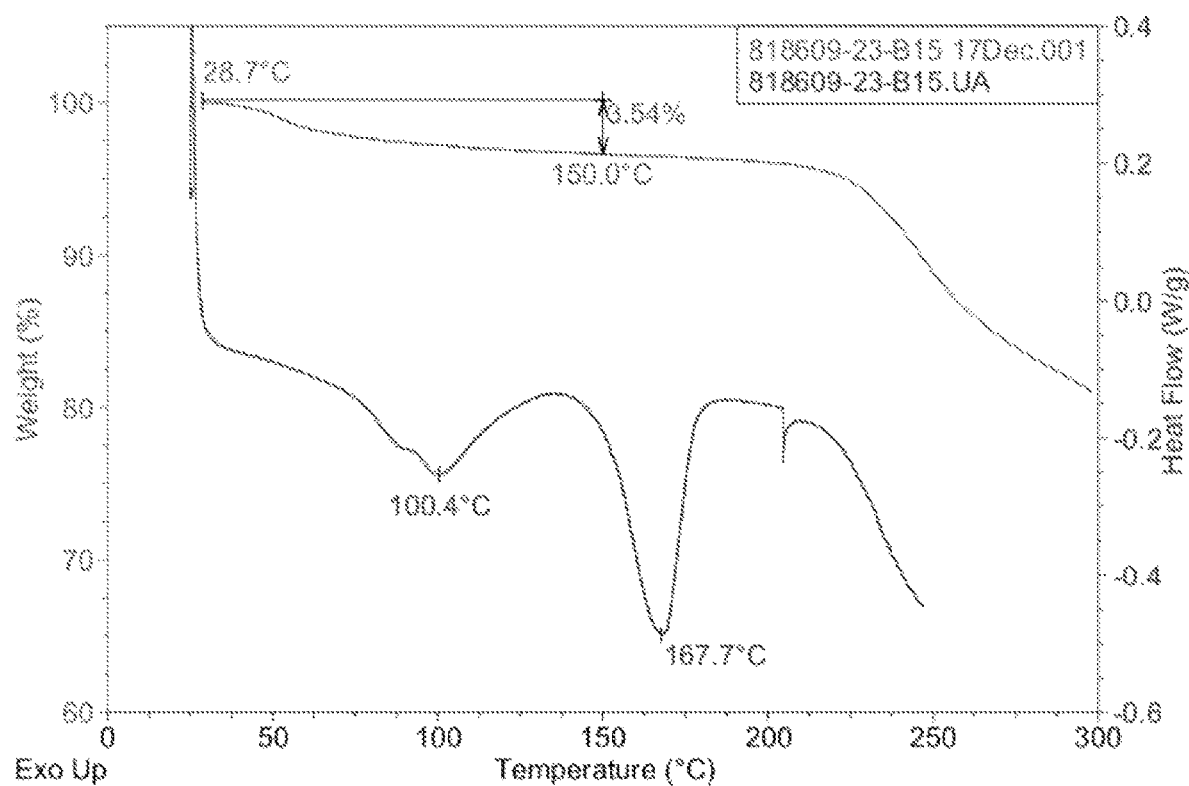
FIG. 14 shows the TGA/DSC thermograms of crystal form C of p-toluenesulfonate.
Figure 22:
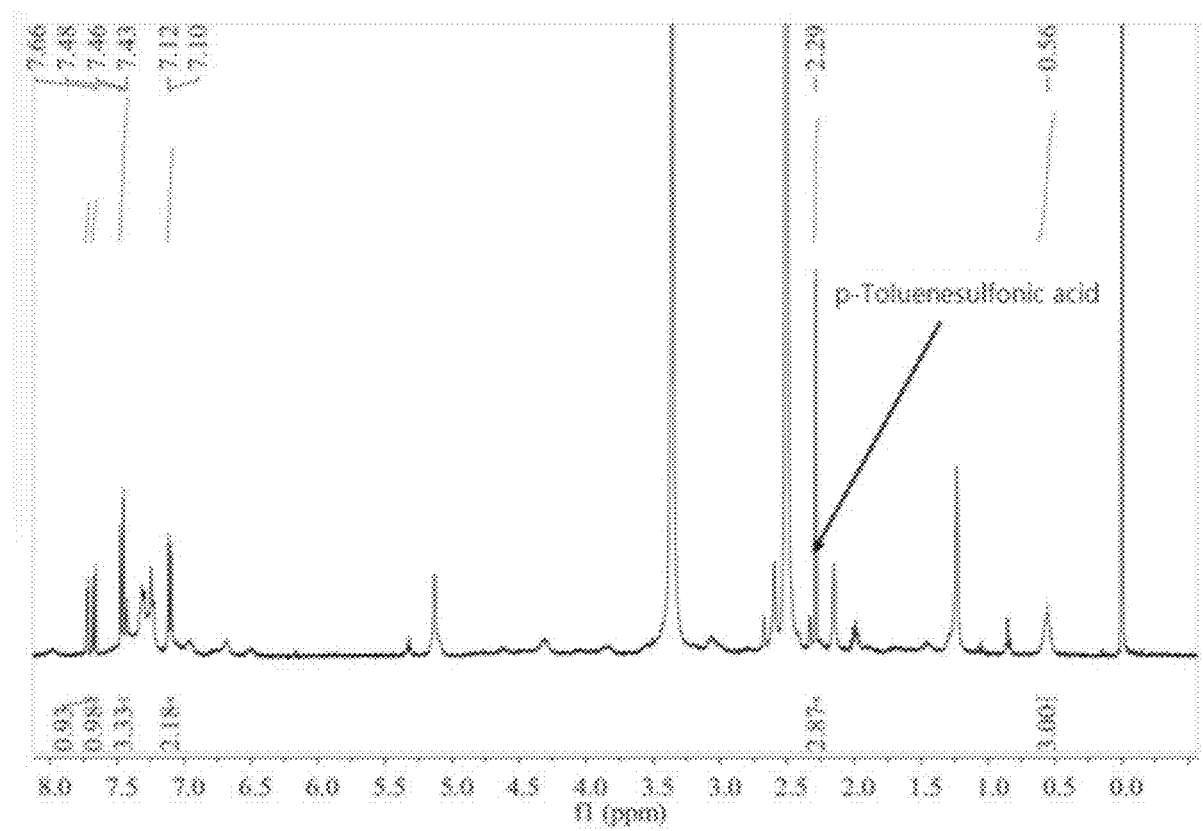
FIG. 22 shows the $^1$H-NMR spectrum of crystal form C of p-toluenesulfonate.

As a specific embodiment, the invention provides a crystal form C of p-toluenesulfonate of OAD2, which has an X-ray powder diffraction pattern comprising peaks at the following diffraction angles (2θ): 4.7±0.2°, 5.4±0.2°, 9.7±0.2°, 13.1±0.2°, 16.4±0.2° and 18.2±0.2°; and preferably, the X-ray powder diffraction pattern comprises substantially the same peaks at the 2θ diffraction angles as shown in FIG. 3, and the X-ray powder diffraction data is as shown in Table 1. In another embodiment, the crystal form C of p-toluenesulfonate of OAD2 is characterized by an $^1$H NMR spectrum as shown in FIG. 22. In another embodiment, the crystal form C of p-toluenesulfonate of OAD2 is characterized by an endothermic peak at 100.4° C. and/or 167.7° C. as determined by DSC. In another embodiment, the crystal form C of p-toluenesulfonate of OAD2 is characterized by a DSC profile as showing in FIG. 14. In another embodiment, the crystal form C of p-toluenesulfonate of OAD2 is characterized by a TGA profile as shown in FIG. 14. In another embodiment, the crystal form C of p-toluenesulfonate of OAD2 is characterized by at least two of the following features:
  i) an XRPD pattern comprising peaks at the following diffraction angles (2θ): 4.7±0.2°, 5.4±0.2°, 9.7±0.2°, 13.1±0.2°, 16.4±0.2° and 18.2±0.2°;
  ii) a DSC profile as shown in FIG. 14;
  iii) a TGA profile as shown in FIG. 14; or
  iv) a $^1$H NMR substantially similar to FIG. 22.

Tartrate

Figure 4:
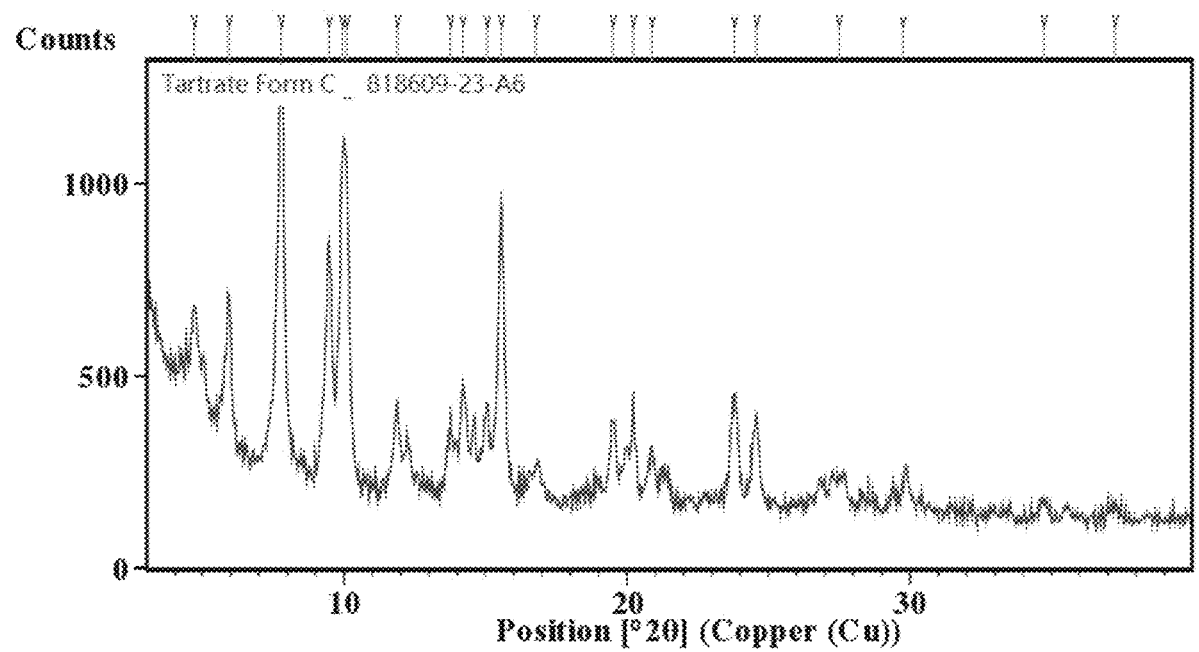
FIG. 4 shows the XRPD of crystal form C of tartrate.
Figure 15:
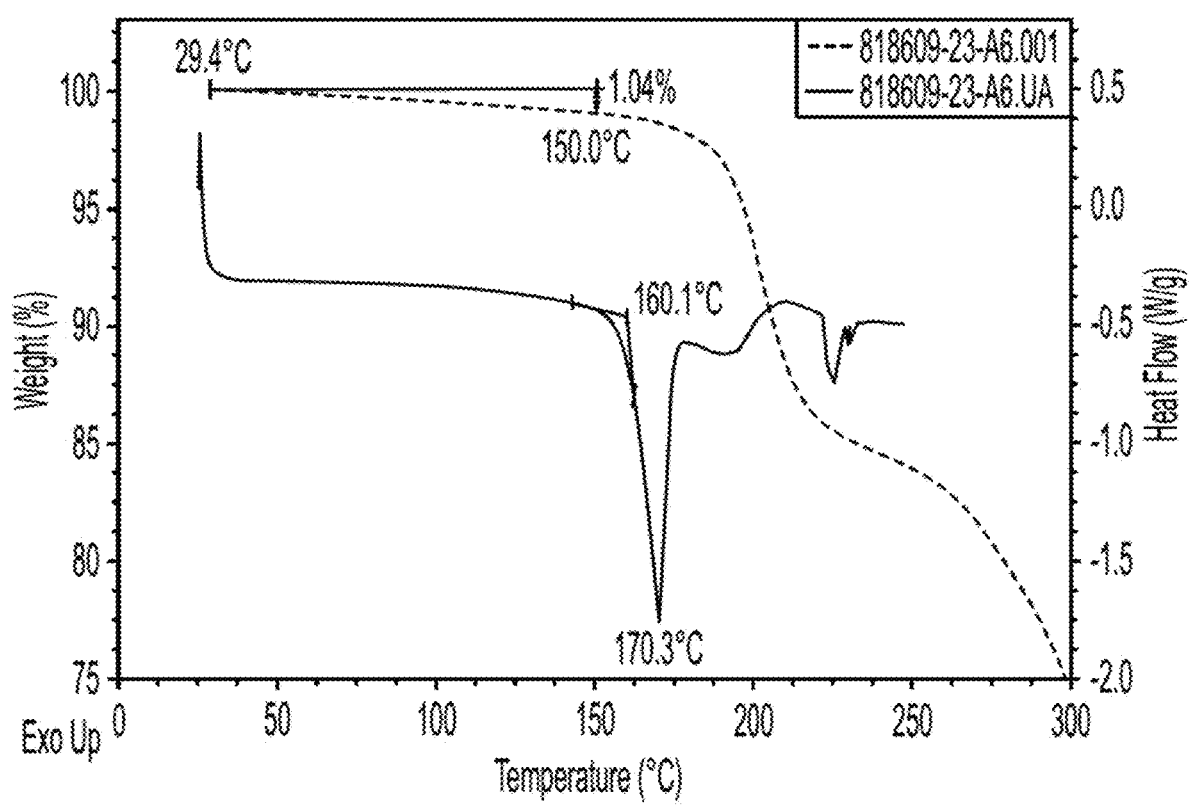
FIG. 15 shows the TGA/DSC thermograms of crystal form C of tartrate.
Figure 23:
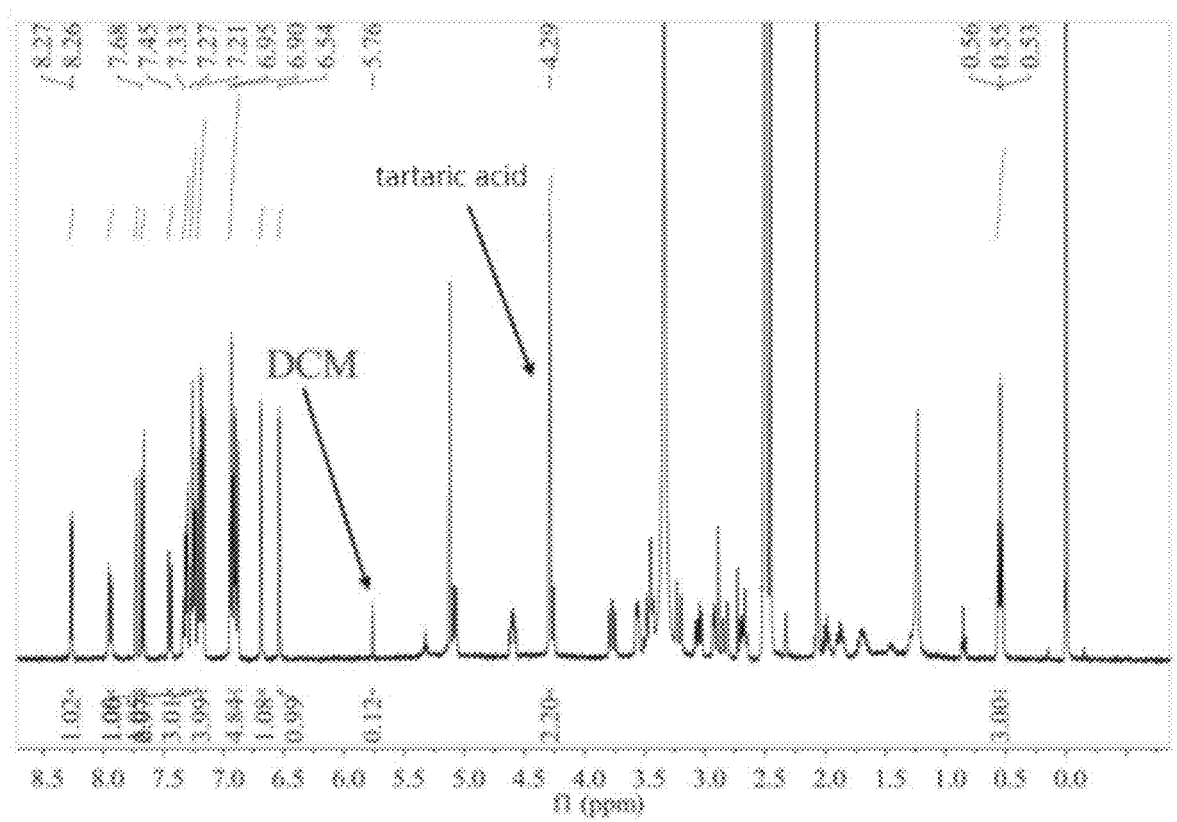
FIG. 23 shows the $^1$H-NMR spectrum of crystal form C of tartrate.

As a specific embodiment, the invention provides a crystal form C of tartrate of OAD2, which has an X-ray powder diffraction pattern comprising peaks at the following diffraction angles (2θ): 7.8±0.2°, 9.9±0.2°, 10.1±0.2°, and 15.6±0.2°; and preferably, the X-ray powder diffraction pattern comprises substantially the same peaks at the 2θ diffraction angles as shown in FIG. 4, and the X-ray powder diffraction data is as shown in Table 1. In another embodiment, the crystal form C of tartrate of OAD2 is characterized by an $^1$H NMR spectrum as shown in FIG. 23. In another embodiment, the crystal form C of tartrate of OAD2 is characterized by an endothermic peak at 170.3° C. as determined by DSC. In another embodiment, the crystal form C of tartrate of OAD2 is characterized by a DSC profile as showing in FIG. 15. In another embodiment, the crystal form C of tartrate of OAD2 is characterized by a TGA profile as shown in FIG. 15. In another embodiment, the crystal form C of tartrate of OAD2 is characterized by at least two of the following features:
  i) an XRPD pattern comprising peaks at the following diffraction angles (2θ): 7.8±0.2°, 9.9±0.2°, 10.1±0.2°, and 15.6±0.2°;
  ii) a DSC profile as shown in FIG. 15;
  iii) a TGA profile as shown in FIG. 15;
  iv) a $^1$H NMR substantially similar to 23.

Citrate

Figure 5:
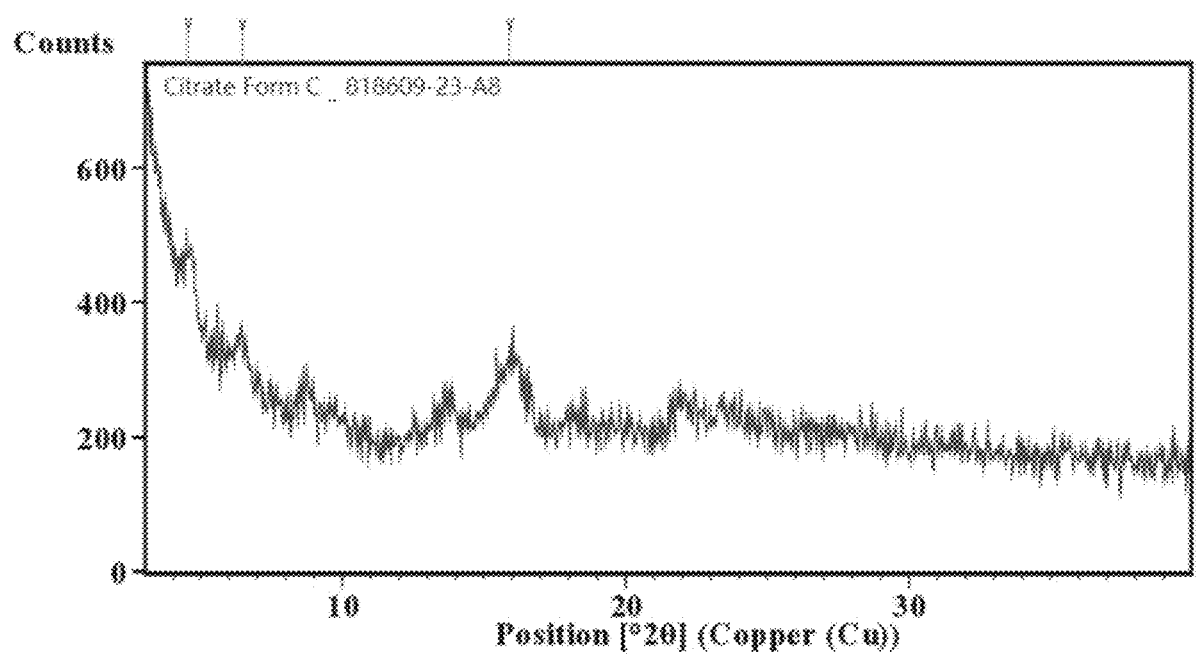
FIG. 5 shows the XRPD of crystal form C of citrate.
Figure 16:
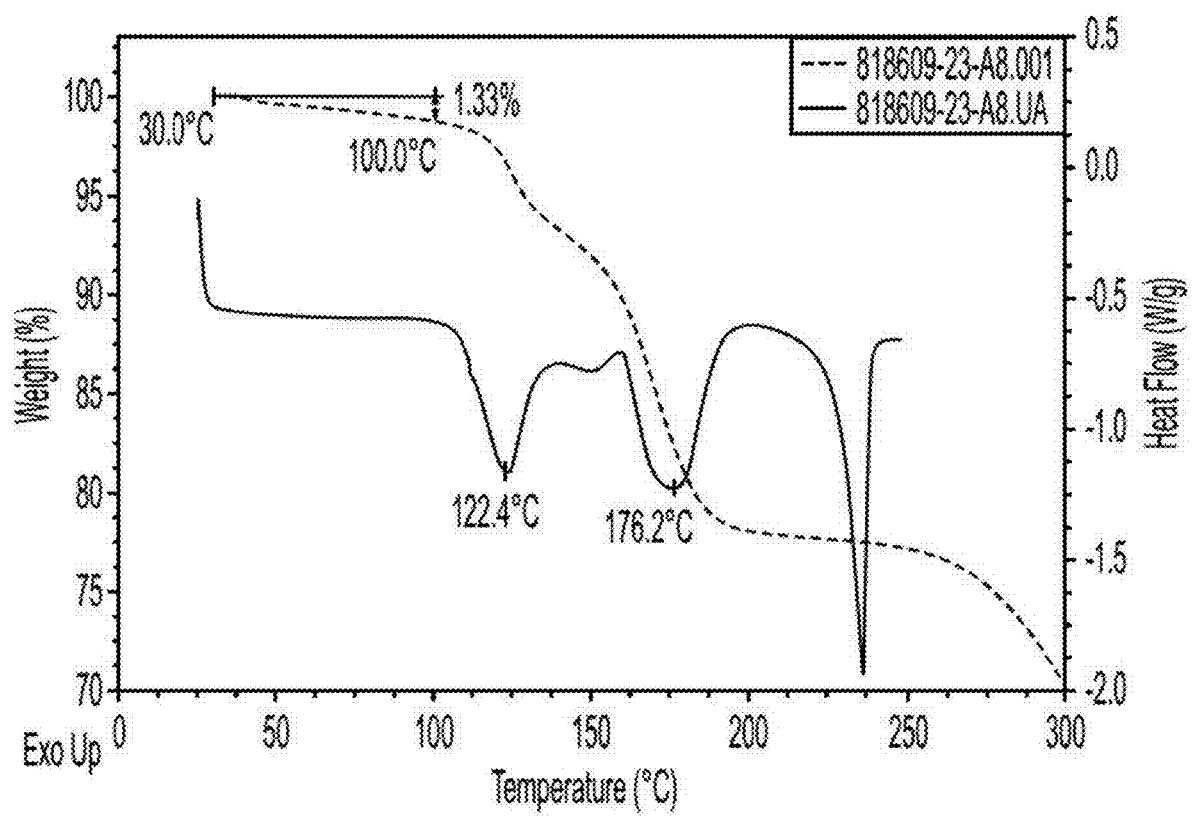
FIG. 16 shows the TGA/DSC thermograms of crystal form C of citrate.
Figure 24:
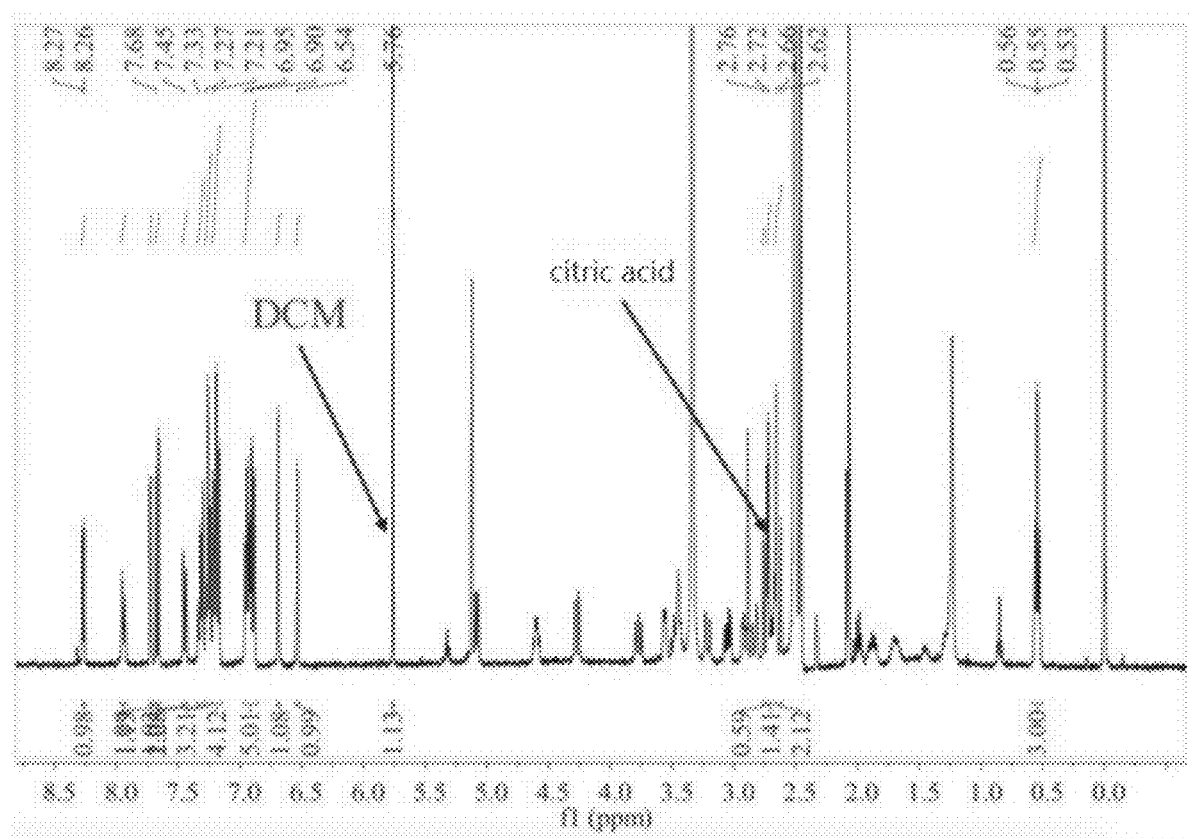
FIG. 24 shows the $^1$H-NMR spectrum of crystal form C of citrate.

As a specific embodiment, the invention provides a crystal form C of citrate of OAD2, which has an X-ray powder diffraction pattern comprising peaks at the following diffraction angles (2θ): 4.5±0.2°, 6.5±0.2°, and 15.9±0.2°; and preferably, the X-ray powder diffraction pattern comprises substantially the same peaks at the 2θ diffraction angles as shown in FIG. 5, and the X-ray powder diffraction data is as shown in Table 1. In another embodiment, the crystal form C of citrate of OAD2 is characterized by an $^1$H NMR spectrum as shown in FIG. 24. In another embodiment, the crystal form C of citrate of OAD2 is characterized by an endothermic peak at 122.4° C. and/or 176.2° C. as determined by DSC. In another embodiment, the crystal form C of citrate of OAD2 is characterized by a DSC profile as showing in FIG. 16. In another embodiment, the crystal form C of citrate of OAD2 is characterized by a TGA profile as shown in FIG. 16. In another embodiment, the crystal form C of citrate of OAD2 is characterized by at least two of the following features:
i) an XRPD pattern comprising peaks at the following diffraction angles (2θ): 4.5±0.2°, 6.5±0.2°, and 15.9±0.2°;
ii) a DSC profile as shown in FIG. 16;
iii) a TGA profile as shown in FIG. 16; or
iv) a $^1$H NMR substantially similar to 24.

Glycollate

Figure 6:
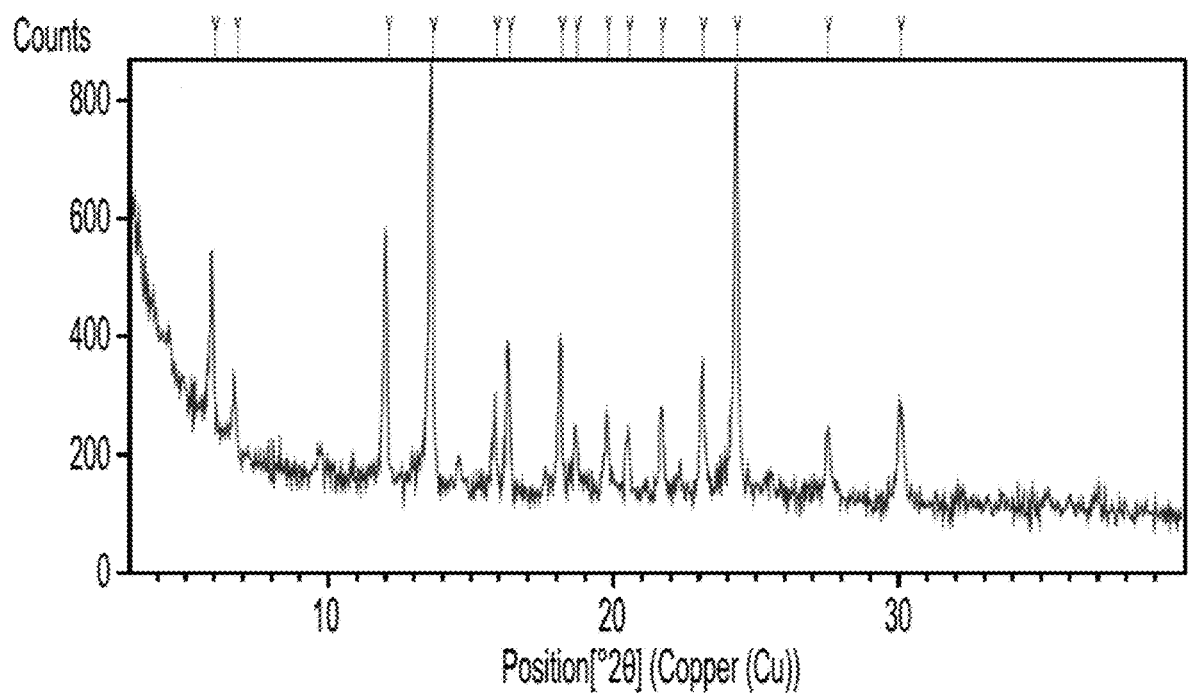
FIG. 6 shows the XRPD of crystal form C of glycollate.
Figure 17:
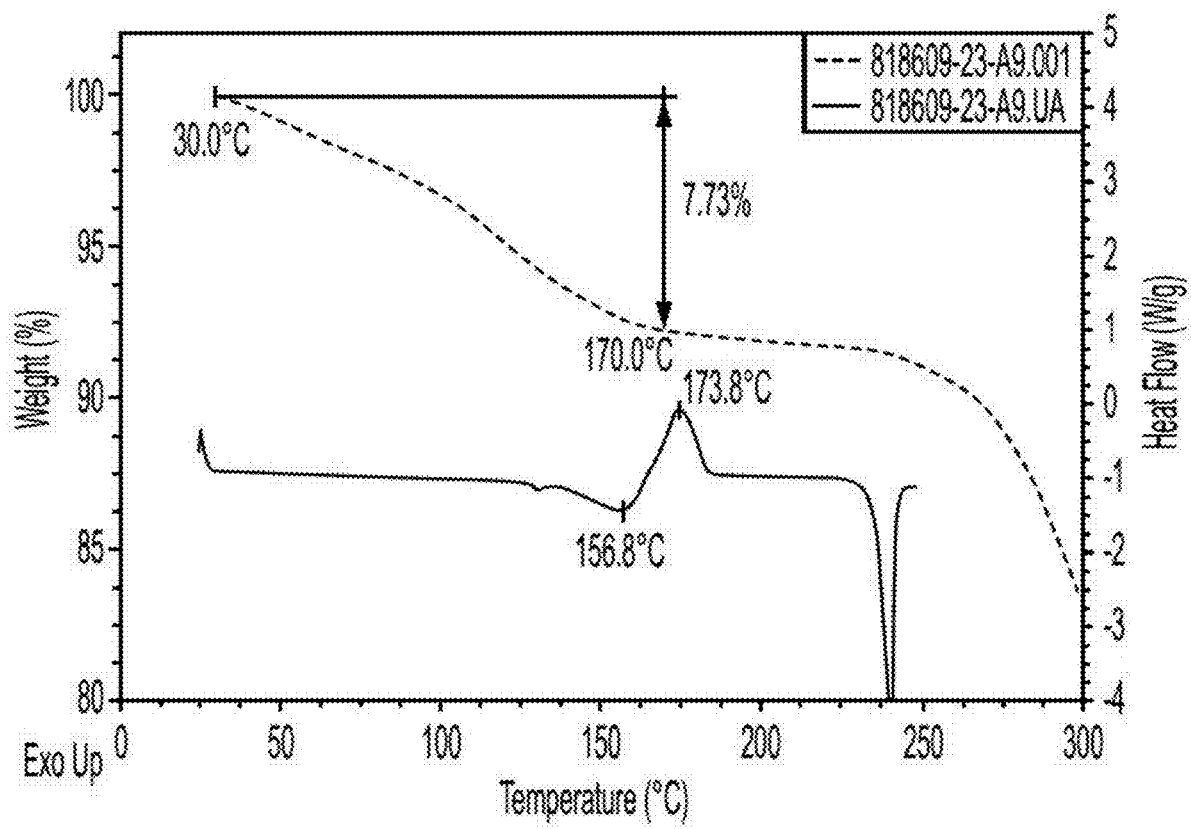
FIG. 17 shows the TGA/DSC thermograms of crystal form C of glycollate.
Figure 25:
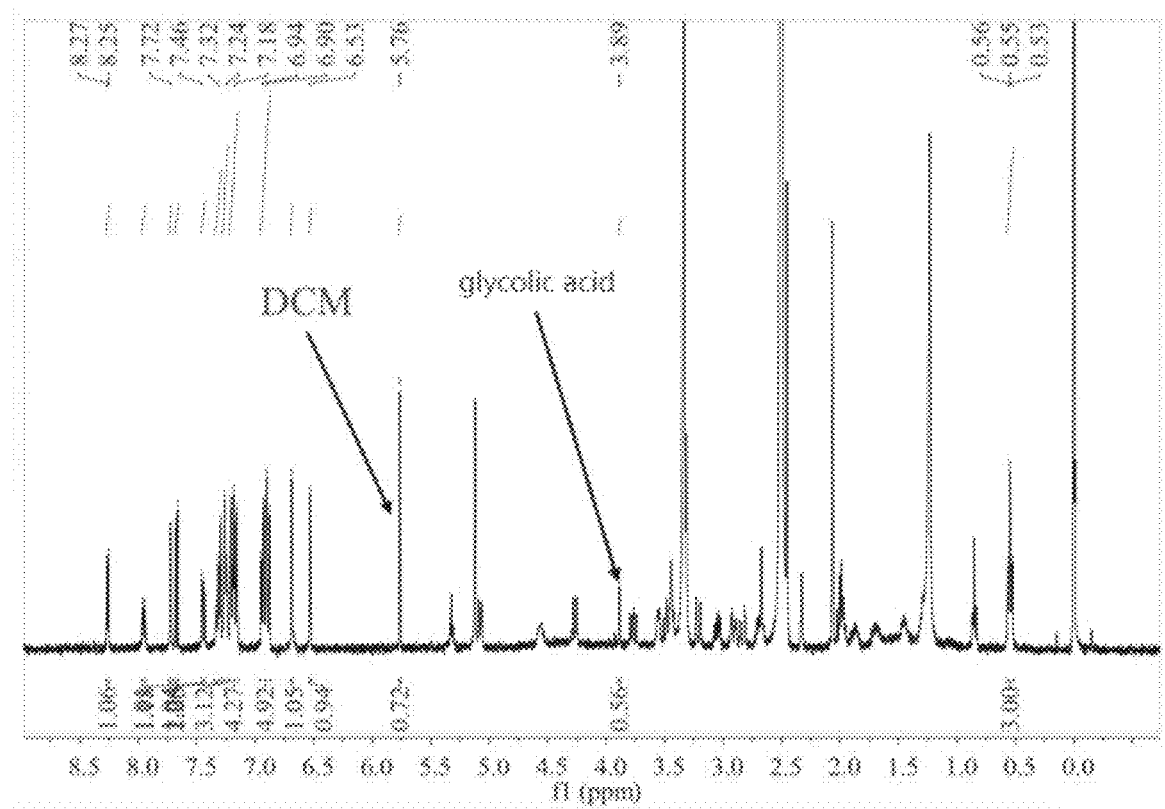
FIG. 25 shows the $^1$H-NMR spectrum of crystal form C of glycollate.

As a specific embodiment, the invention provides a crystal form C of glycollate of OAD2, which has an X-ray powder diffraction pattern comprising peaks at the following diffraction angles (2θ): 6.0±0.2°, 12.1±0.2°, 13.6±0.2°, 18.2±0.2° and 24.3±0.2°; and preferably, the X-ray powder diffraction pattern comprises substantially the same peaks at the 2θ diffraction angles as shown in FIG. 6, and the X-ray powder diffraction data is as shown in Table 1. In another embodiment, the crystal form C of glycollate of OAD2 is characterized by an $^1$H NMR spectrum as shown in FIG. 25. In another embodiment, the crystal form C of glycollate of OAD2 is characterized by an endothermic peak at 156.8° C. and/or 173.8° C. as determined by DSC. In another embodiment, the crystal form C of glycollate of OAD2 is characterized by a DSC profile as showing in FIG. 17. In another embodiment, the crystal form C of glycollate of OAD2 is characterized by a TGA profile as shown in FIG. 17. In another embodiment, the crystal form C of glycollate of OAD2 is characterized by at least two of the following features:
i) an XRPD pattern comprising peaks at the following diffraction angles (2θ): 6.0±0.2°, 12.1±0.2°, 13.6±0.2°, 18.2±0.2° and 24.3±0.2°;
ii) a DSC profile as shown in FIG. 17;
iii) a TGA profile as shown in FIG. 17; or
iv) a $^1$H NMR substantially similar to 25.

Methanesulfonate

Figure 7:
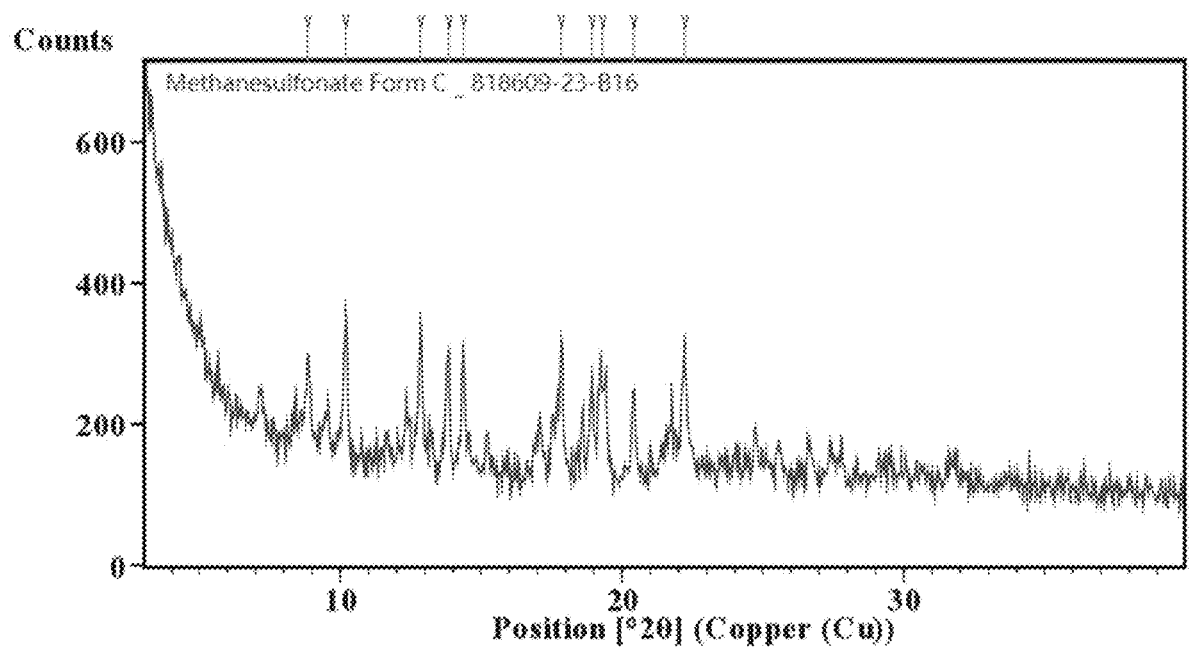
FIG. 7 shows the XRPD of crystal form C of methanesulfonate.
Figure 18:
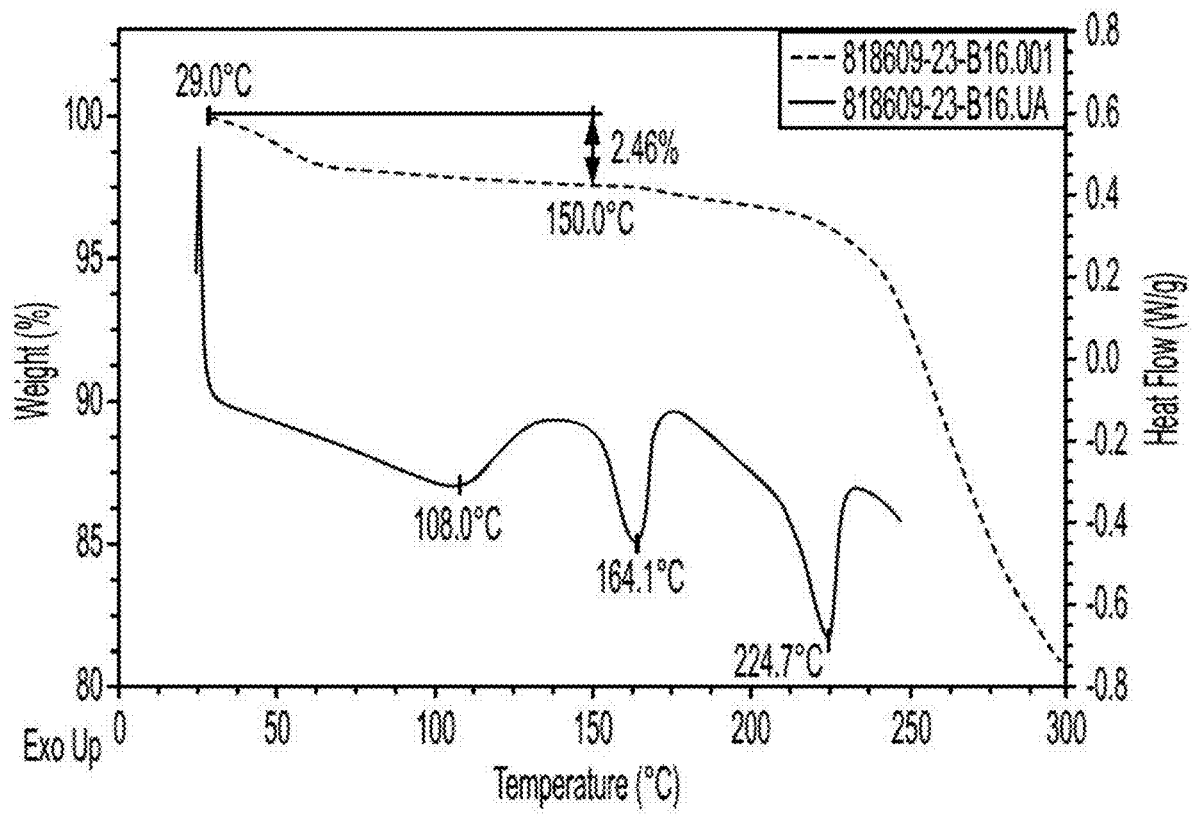
FIG. 18 shows the TGA/DSC thermograms of crystal form C of methanesulfonate.
Figure 26:
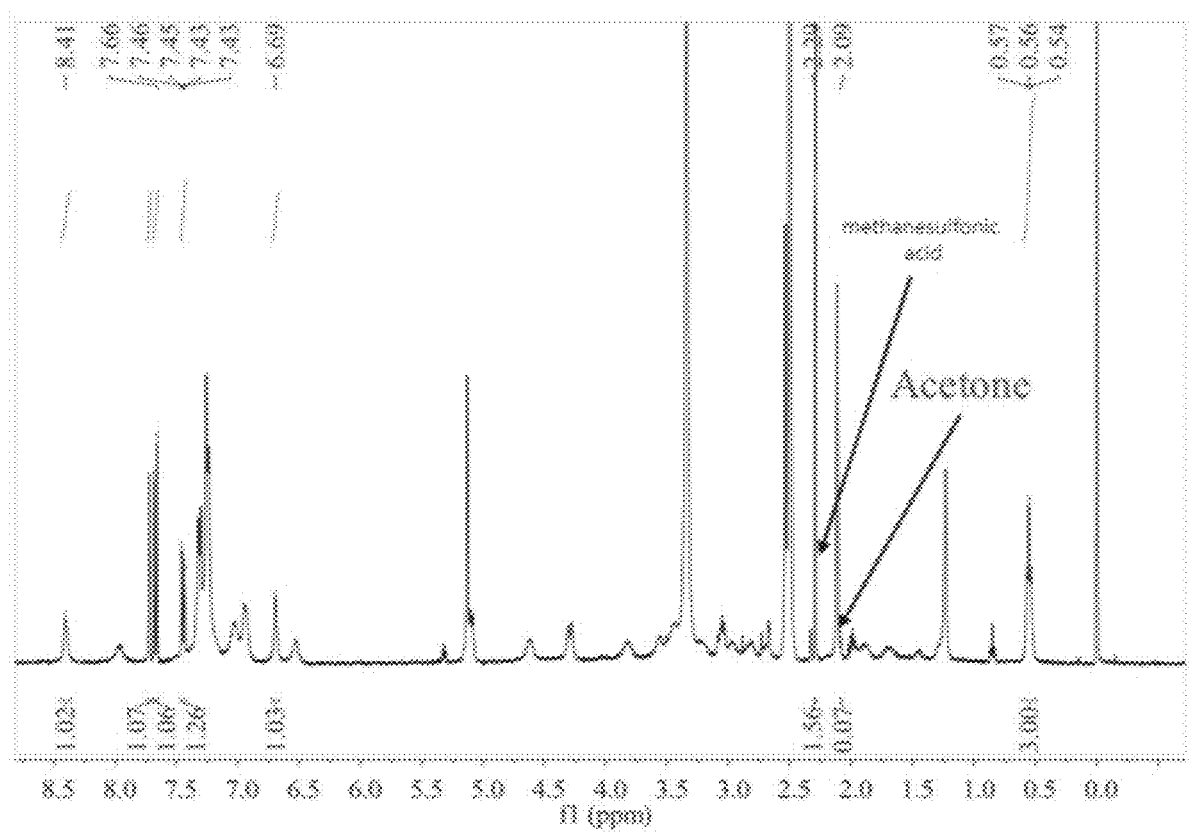
FIG. 26 shows the $^1$H-NMR spectrum of crystal form C of methanesulfonate.

As a specific embodiment, the invention provides a crystal form C of methanesulfonate of OAD2, which has an X-ray powder diffraction pattern comprising peaks at the following diffraction angles (2θ): 10.2±0.2°, 12.8±0.2°, 13.8±0.2°, 14.4±0.2° and 22.2±0.2°; and preferably, the X-ray powder diffraction pattern comprises substantially the same peaks at the 2θ diffraction angles as shown in FIG. 7, and the X-ray powder diffraction data is as shown in Table 1. In another embodiment, the crystal form C of methanesulfonate of OAD2 is characterized by an $^1$H NMR spectrum as shown in FIG. 26. In another embodiment, the crystal form C of methanesulfonate of OAD2 is characterized by an endothermic peak at 108.0, 164.1, and/or 224.7° C. as determined by DSC. In another embodiment, the crystal form C of methanesulfonate of OAD2 is characterized by a DSC profile as showing in FIG. 18. In another embodiment, the crystal form C of methanesulfonate of OAD2 is characterized by a TGA profile as shown in FIG. 18. In another embodiment, the crystal form C of methanesulfonate of OAD2 is characterized by at least two of the following features:
i) an XRPD pattern comprising peaks at the following diffraction angles (2θ): 10.2±0.2°, 12.8±0.2°, 13.8±0.2°, 14.4±0.2° and 22.2±0.2°;
ii) a DSC profile as shown in FIG. 18;
iii) a TGA profile as shown in FIG. 18; or
iv) a $^1$H NMR substantially similar to 26.

Hydrobromide

Figure 8:
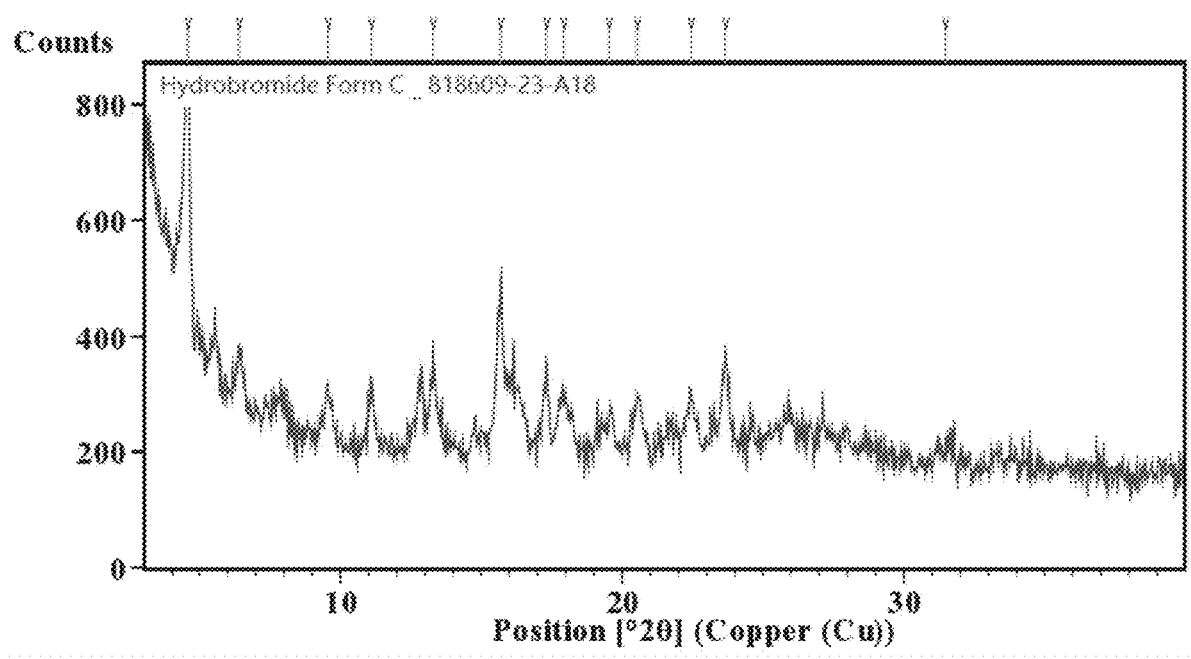
FIG. 8 shows the XRPD of crystal form C of hydrobromide.
Figure 19:
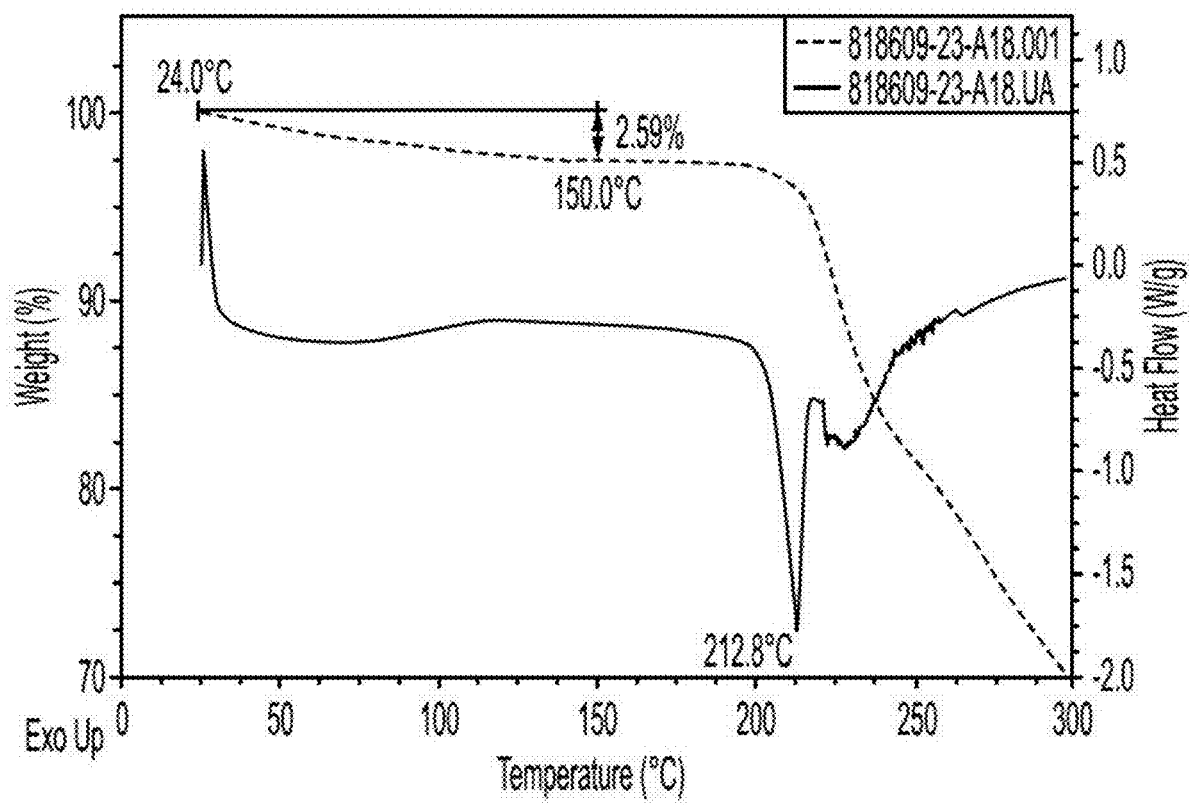
FIG. 19 shows the TGA/DSC thermograms of crystal form C of hydrobromide.

As a specific embodiment, the invention provides a crystal form C of hydrobromide of OAD2, which has an X-ray powder diffraction pattern comprising peaks at the following diffraction angles (2θ): 4.6±0.2°, 15.7±0.2°, and 23.7±0.2°; and preferably, the X-ray powder diffraction pattern comprises substantially the same peaks at the 2θ diffraction angles as shown in FIG. 8, and the X-ray powder diffraction data is as shown in Table 1. In another embodiment, the crystal form C of hydrobromide of OAD2 is characterized by an $^1$H NMR spectrum. In another embodiment, the crystal form C of hydrobromide of OAD2 is characterized by an endothermic peak at 212.8° C. as determined by DSC. In another embodiment, the crystal form C of hydrobromide of OAD2 is characterized by a DSC profile as showing in FIG. 19. In another embodiment, the crystal form C of hydrobromide of OAD2 is characterized by a TGA profile as shown in FIG. 19. In another embodiment, the crystal form C of hydrobromide of OAD2 is characterized by at least two of the following features:
i) an XRPD pattern comprising peaks at the following diffraction angles (2θ): 4.6±0.2°, 15.7±0.2°, and 23.7±0.2°;
ii) a DSC profile as shown in FIG. 19; or
iii) a TGA profile as shown in FIG. 19.

Figure 9:
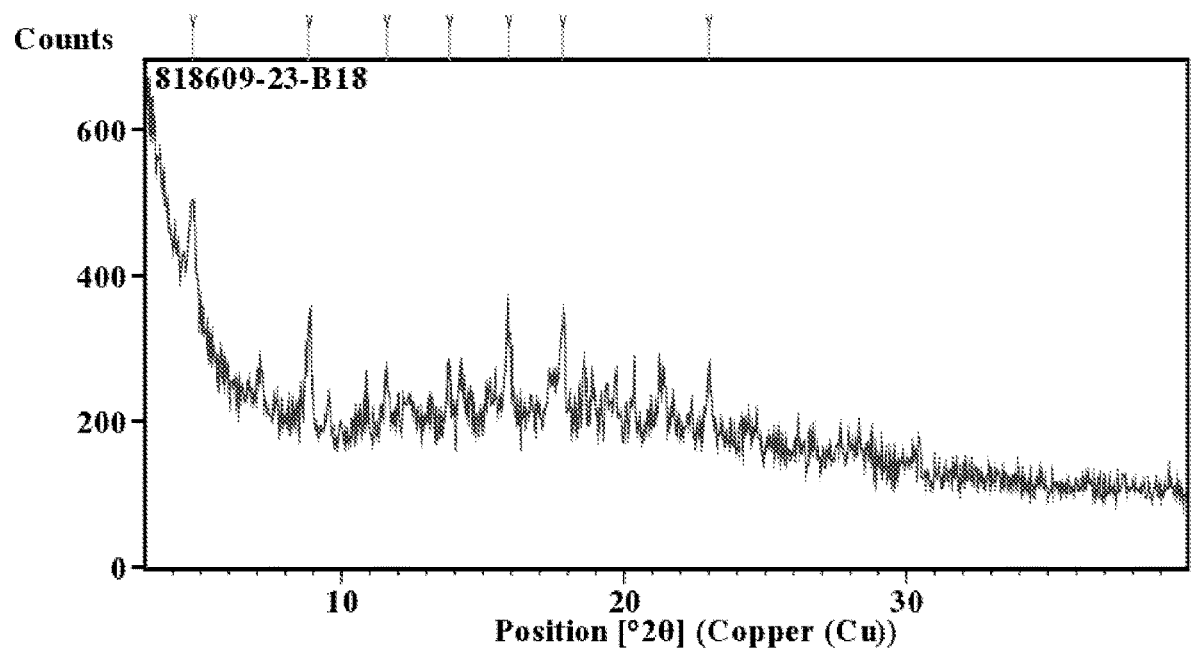
FIG. 9 shows the XRPD of crystal form D of hydrobromide.
Figure 20:
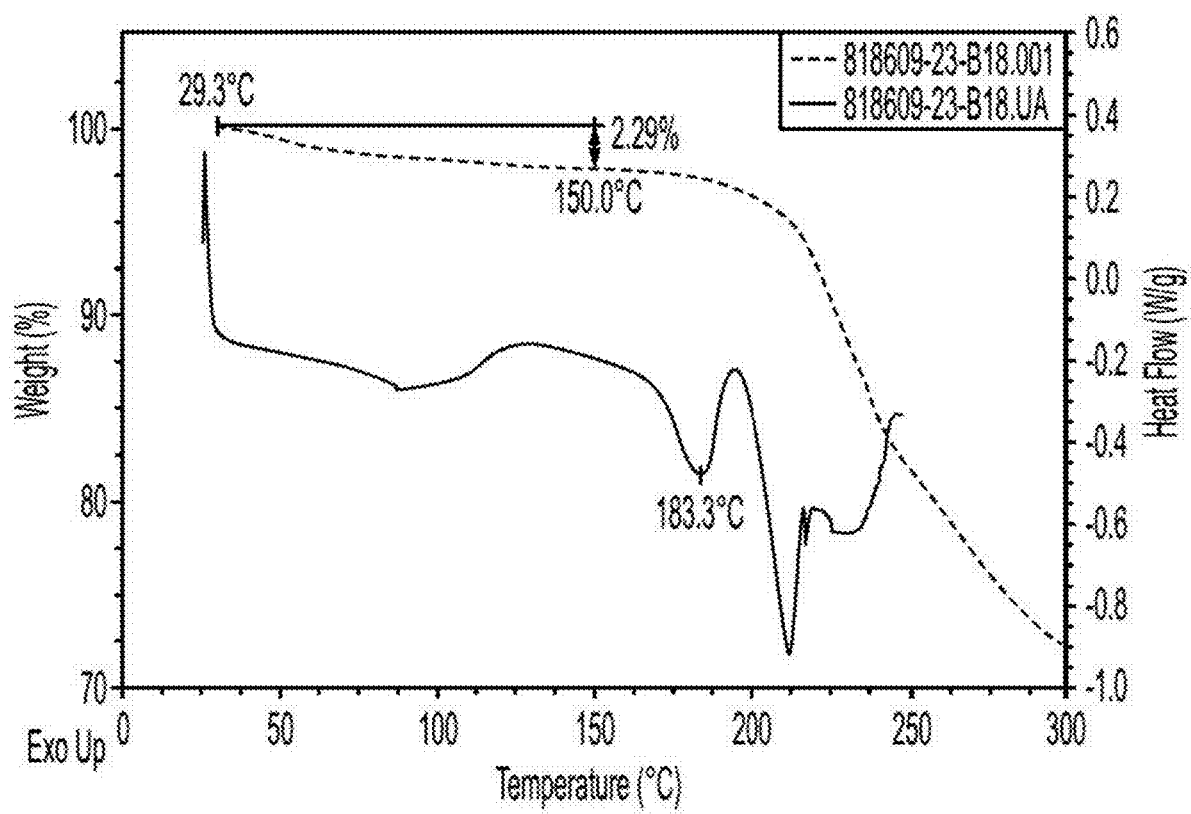
FIG. 20 shows the TGA/DSC thermograms of crystal form D of hydrobromide.

As a specific embodiment, the invention provides a crystal form D of hydrobromide of OAD2, which has an X-ray powder diffraction pattern comprising peaks at the following diffraction angles (2θ): 4.7±0.2°, 8.8±0.2°, 15.9±0.2°, and 17.8±0.2°; and preferably, the X-ray powder diffraction pattern comprises substantially the same peaks at the 2θ diffraction angles as shown in FIG. 9, and the X-ray powder diffraction data is as shown in Table 1. In another embodiment, the crystal form D of hydrobromide of OAD2 is characterized by an $^1$H NMR spectrum. In another embodiment, the crystal form D of hydrobromide of OAD2 is characterized by an endothermic peak at 183.3° C. as determined by DSC. In another embodiment, the crystal form D of hydrobromide of OAD2 is characterized by a DSC profile as showing in FIG. 20. In another embodiment, the crystal form D of hydrobromide of OAD2 is characterized by a TGA profile as shown in FIG. 20. In another embodiment, the crystal form D of hydrobromide of OAD2 is characterized by at least two of the following features:
i) an XRPD pattern comprising peaks at the following diffraction angles (2θ): 4.7±0.2°, 8.8±0.2°, 15.9±0.2°, and 17.8±0.2°;
ii) a DSC profile as shown in FIG. 20; or
iii) a TGA profile as shown in FIG. 20.

Sulfate

Figure 10:
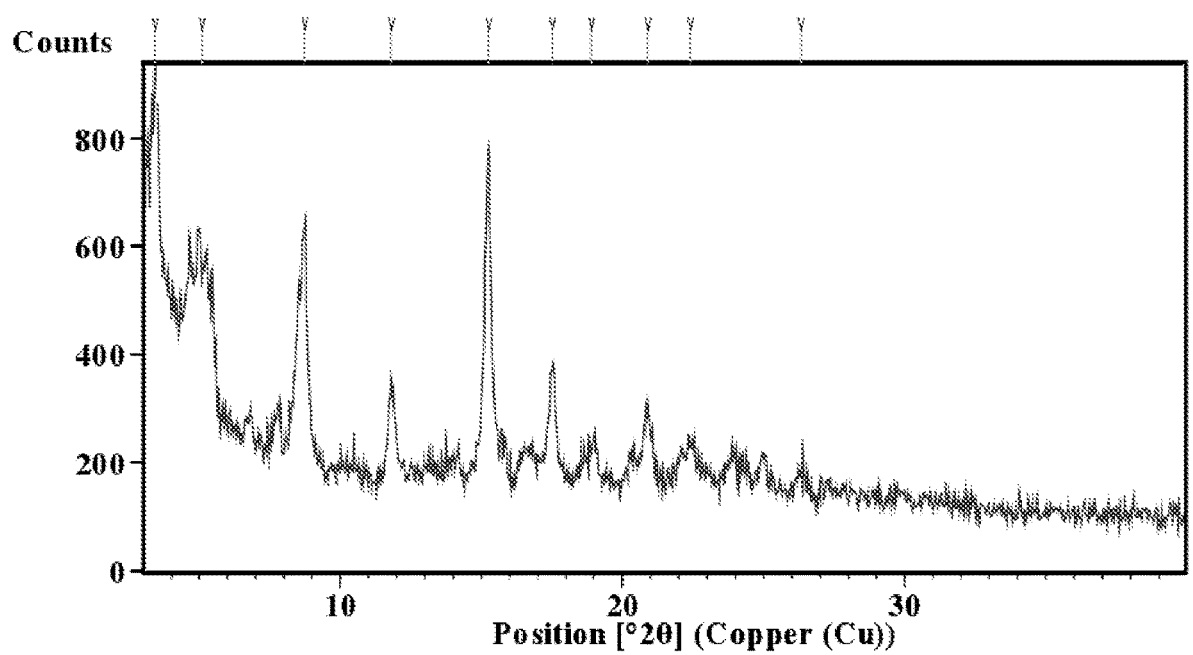
FIG. 10 shows the XRPD of crystal form C of sulfate.
Figure 21:
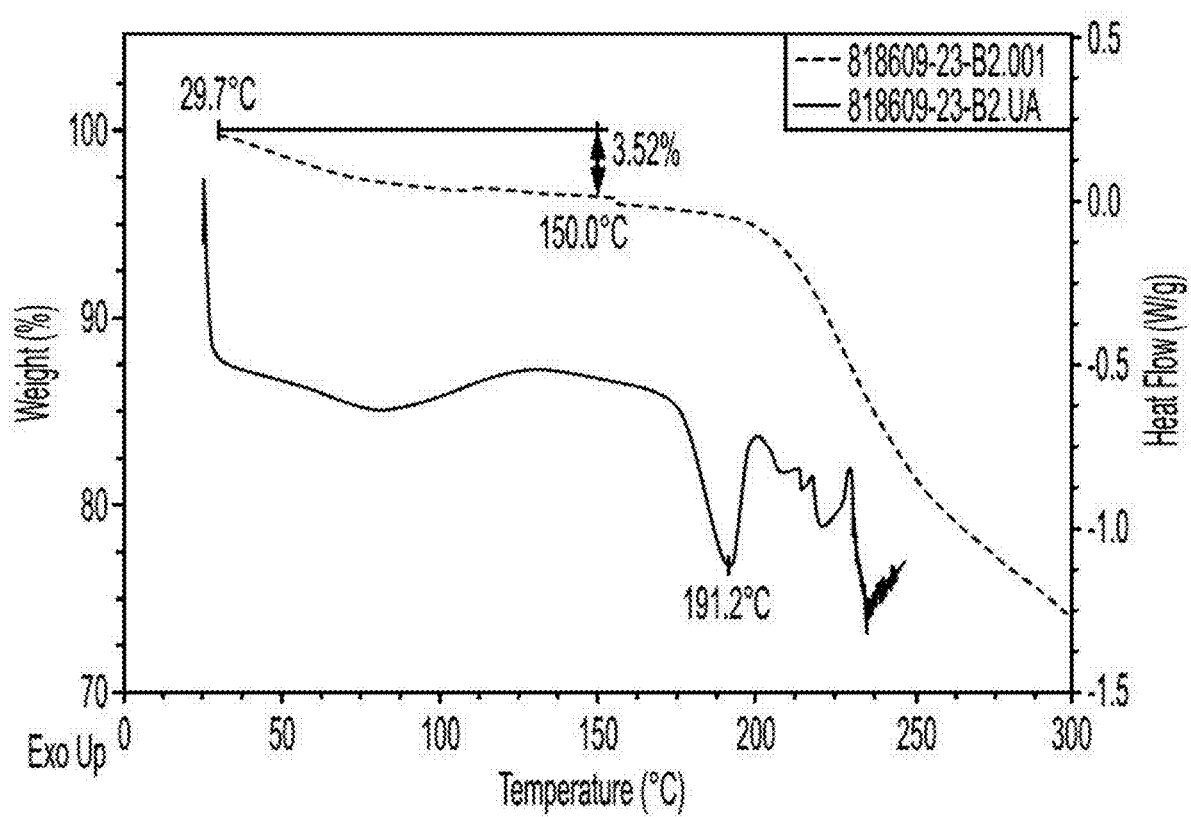
FIG. 21 shows the TGA/DSC thermograms of crystal form C of sulfate.

As a specific embodiment, the invention provides a crystal form C of sulfate of OAD2, which has an X-ray powder diffraction pattern comprising peaks at the following diffraction angles (2θ): 3.4±0.2°, 8.7±0.2°, and 15.2±0.2°; and preferably, the X-ray powder diffraction pattern comprises substantially the same peaks at the 2θ diffraction angles as shown in FIG. 10, and the X-ray powder diffraction data is as shown in Table 1. In another embodiment, the crystal form C of sulfate of OAD2 is characterized by an $^1$H NMR spectrum. In another embodiment, the crystal form C of sulfate of OAD2 is characterized by an endothermic peak at 191.2° C. as determined by DSC. In another embodiment, the crystal form C of sulfate of OAD2 is characterized by a DSC profile as showing in FIG. 21. In another embodiment, the crystal form C of sulfate of OAD2 is characterized by a TGA profile as shown in FIG. 21. In another embodiment, the crystal form C of sulfate of OAD2 is characterized by at least two of the following features:
 i) an XRPD pattern comprising peaks at the following diffraction angles (2θ): 3.4±0.2°, 8.7±0.2°, and 15.2±0.2°;
 ii) a DSC profile as shown in FIG. 21; or
 iii) a TGA profile as shown in FIG. 21.

TABLE 1

X-ray diffraction data (2θ) of crystalline acid salts of OAD2

| Crystal form | 2θ (±0.2°) | | | | | | |
|---|---|---|---|---|---|---|---|
| Crystal form B of hydrochloride | 4.5 | 5.3 | 5.9 | 9.2 | 10.3 | 10.7 | 12.0 |
| | 12.4 | 12.9 | 13.2 | 14.8 | 15.5 | 15.9 | 17.8 |
| | 19.9 | 20.6 | 21.7 | 24.0 | 24.6 | 26.7 | 27.2 |
| Crystal form C of hydrochloride | 4.8 | 7.1 | 8.9 | 11.6 | 12.8 | 14.3 | 15.3 |
| | 15.9 | 17.5 | 18.7 | 19.8 | 21.2 | 22.4 | 23.1 |
| | 24.5 | 28.6 | 30.4 | / | / | / | / |
| Crystal form C of p-toluenesulfonate | 4.7 | 5.4 | 9.3 | 9.7 | 10.9 | 12.4 | 13.1 |
| | 16.4 | 17.3 | 18.2 | 19.7 | 20.6 | 23.5 | 25.0 |
| | 25.6 | 29.0 | / | / | / | / | / |
| Crystal form C of tartrate | 4.7 | 5.9 | 7.8 | 9.5 | 9.9 | 10.1 | 11.9 |
| | 13.7 | 14.2 | 15.0 | 15.6 | 16.8 | 19.5 | 20.2 |
| | 20.9 | 23.8 | 24.6 | 27.5 | 29.8 | / | / |
| Crystal form C of citrate | 4.5 | 6.5 | 15.9 | / | / | / | / |
| Crystal form C of glycollate | 6.0 | 6.8 | 12.1 | 13.6 | 15.9 | 16.4 | 18.2 |
| | 18.7 | 19.8 | 20.5 | 21.7 | 23.1 | 24.3 | 27.5 |
| | 30.0 | / | / | / | / | / | / |
| Crystal form C of methanesulfonate | 8.8 | 10.2 | 12.8 | 13.8 | 14.4 | 17.8 | 18.9 |
| | 19.3 | 20.4 | 22.2 | / | / | / | / |
| Crystal form C of hydrobromide | 4.6 | 6.4 | 9.6 | 11.1 | 13.3 | 15.7 | 17.3 |
| | 17.9 | 19.5 | 20.5 | 22.4 | 23.7 | / | / |
| Crystal form D of hydrobromide | 4.7 | 8.8 | 11.6 | 13.8 | 15.9 | 17.8 | 23.0 |
| Crystal form C of sulfate | 3.4 | 5.1 | 8.7 | 11.8 | 15.2 | 17.5 | 18.9 |
| | 20.9 | 22.4 | 26.3 | / | / | / | / |

Pharmaceutical Compositions

The invention further provides a pharmaceutical composition comprising one or more pharmaceutically acceptable acid salt forms of OAD2, and optionally a pharmaceutical acceptable carrier. In another embodiment, the invention provides a pharmaceutical composition comprising a crystalline, pharmaceutically acceptable acid salt of OAD2, wherein the pharmaceutical composition comprises a therapeutically effective amount of the crystalline, pharmaceutically acceptable acid salt of OAD2, and optionally a pharmaceutical acceptable carrier.

In another embodiment, the pharmaceutical composition of the invention comprises a pharmaceutically acceptable acid salt formed between OAD2 and a pharmaceutically acceptable acid. In one embodiment, the pharmaceutically acceptable acid is selected from the group consisting of 1-hydroxy-2-naphthoic acid, 4-aminosalicylic acid, adipic acid, L-aspartic acid, benzene sulfonic acid, benzoic acid, trans-cinnamic acid, citric acid, fumaric acid, galactaric acid, gentisic acid, gluconic acid, glutamic acid, glutaric acid, glycolic acid, hexanoic acid, hippuric acid, hydrobromic acid, hydrochloric acid, L-lactic acid, maleic acid, L-malic acid, malonic acid, R-mandelic acid, methane sulfonic acid, naphthalene sulfonic acid, nicotinic acid, oxalic acid, palmitic acid, phosphoric acid, propionic acid, saccharin, salicyclic acid, stearic acid, succinic acid, sulfuric acid, L-tartaric acid, p-toluenesulfonic acid, vanillic acid, and vanillin. In another embodiment, the pharmaceutically acceptable acid is selected from the group consisting of hydrobromic acid, hydrochloric acid, p-toluenesulfonic acid, tartaric acid, citric acid, glycolic acid, methanesulfonic acid, and sulfonic acid.

The pharmaceutical composition may be prepared according to methods known in the art. Preferably, the crystalline acid salts of OAD2 of the invention is 0.001%~99% by weight of the pharmaceutical composition. As a specific embodiment, the crystalline acid salt of OAD2 is combined with one or more pharmaceutically acceptable carriers and formulated into any dosage form that is suitable for use in human or non-human animals.

Pharmaceutical compositions of the present invention comprising a pharmaceutically acceptable acid salt of OAD2 may be in a form suitable for oral use, for example, as tablets, troches, lozenges, dispersible powders or granules, or hard or soft capsules. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations.

Tablets, tronches, lozenges, dispersible powders or granules, or hard or soft capsules may contain a pharmaceutically acceptable acid salt of OAD2 in admixture with one or more pharmaceutically-acceptable carriers which are suitable for the manufacture of such tablets, tronches, lozenges, dispersible powders or granules, or hard or soft capsules.

A "pharmaceutically acceptable carrier" is a medium generally accepted in the art for the delivery of biologically active agents to mammals, e.g., humans. Such carriers are generally formulated according to a number of factors well within the purview of those of ordinary skill in the art to determine and account for. These include, without limitation, the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources.

Methods of Treatment

In another aspect, the present invention provides pharmaceutical compositions comprising a therapeutically effective amount of a pharmaceutically acceptable acid salt of OAD2 wherein a therapeutically effective amount of a pharmaceutically acceptable acid salt OAD2 comprises a sufficient amount for the treatment of a condition or disorder where activation of the GLP-1 receptor is beneficial.

In another aspect, the present invention also provides a method of treatment comprising administering a therapeutically effective amount of a pharmaceutically acceptable salt of OAD2 to a human in need thereof. The method may comprise administering a pharmaceutical composition comprising a therapeutically effective amount of a pharmaceutically acceptable acid salt of OAD2 to a human in need thereof. In another embodiment, the pharmaceutically acceptable salt of OAD2 may be administered in crystalline form.

The methods of treatment may useful to treat a disorder or condition where activation of the GLP-1 receptor is beneficial, such as, but not limited to a disorder or condition is selected from the group consisting of: metabolic syndrome, glucose intolerance, hyperglycemia, dyslipidemia, diabetes mellitus type 1, diabetes mellitus type 2, hypertriglyceridemia, syndrome X, insulin resistance, impaired glucose tolerance (IGT), obesity, diabetic dyslipidemia, hyperlipidemia, arteriosclerosis, atherosclerosis, other cardiovascular diseases, hypertension, metabolic disorders that where activation of the GLP-1 receptor is beneficial, and complications resulting from or associated with diabetes, including, but not limited to, neuropathy, retinopathy, nephropathy, and impaired wound healing. In an embodiment, the condition treated is type 2 diabetes.

A pharmaceutically acceptable acid salt of OAD2 of the present invention may be administered at a dosage level such that the amount of OAD2 administered is between 1 mg and 100 mg per day. The dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination and the severity of the particular disease undergoing therapy.

EXAMPLES

Experimental Instruments and Protocols:
1. X-ray powder diffraction (XRPD): See the table 2 below showing the test parameters.

TABLE 2

XRPD test parameters

| Parameters | Instrument 1 | Instrument 2 | Instrument 3 |
|---|---|---|---|
| Model | Empyrean | X' Pert3 | X' Pert3 |
| X-ray | Cu, Kα, Kα1 (Å: 1.540598, Kα2 (Å: 1.544426 Kα2/Kα1 intensity ratio: 0.50 | Cu, Kα, Kα1 (Å: 1.540598, Kα2 (Å: 1.544426 Kα2/Kα1 intensity ratio: 0.50 | Cu, Kα, Kα1 (Å: 1.540598, Kα2 (Å: 1.544426 Kα2/Kα1 intensity ratio: 0.50 |
| X-ray tube settings | 45 kV, 40 mA | 45 kV, 40 mA | 45 kV, 40 mA |
| Divergence slit | Automatic | 1/8° | 1/8° |
| Scan mode | Continuous | Continuous | Continuous |
| Scan range (°2Theta) | 3-40 | 3-40 | 3-40 |
| Scan time per step (s) | 17.8 | 46.7 | 46.7 |
| Scan step (°2Theta) | 0.0167 | 0.0263 | 0.0263 |
| Measure time | ~5 min 30 s | ~5 min | ~5 min |

2. Thermogravimetric analysis (TGA) and differential scanning calorimetry (DSC) Collected on TA Q5000/5500 thermogravimetric analyzer and TA Q200/Q2000/2500 differential scanning calorimeter, respectively. See the table 3 below showing the test parameters.

TABLE 3

DSC and TGA test parameters

| Parameters | TGA | DSC |
|---|---|---|
| Method | Linear heating | Linear heating |
| Sample | Aluminum plate, open | Aluminum plate, covered/uncovered |
| Temperature | Room temperature-endpoint temperature | 25° C.-endpoint temperature |
| Scan rate (° C./min) | 10 | 10 |
| Gas protection | Nitrogen | Nitrogrn |

3. The liquid NMR was collected on Bruker 400M nuclear magnetic resonance with DMSO-d6 as the solvent.

4. The salt formation molar ratio test of ions is performed by ion chromatography. The test conditions are shown in Table 4.

TABLE 4

Salt formation molar ratio test conditions

| | |
|---|---|
| Ion chromatograph | ThermoFisher ICS-1100 |
| Chromatographic column | IonPac AS18 Analytical Column, 250 * 4 mm (anion) Dionex IonpacTM CS12A RFICTM, 250 * 4 mm (cation) |
| Mobile phase | 25 mM NaOH ((anion), 20 mMMethanesulfonic acid (cation) |
| Sample volume | 25 μL |
| Speed | 1.0 mL/min |
| System temperature | 35° |
| Column | 35° |
| Electric current | 80 mA |
| Running time | Chloride ion 6.0 min, Sulfate ion 10.0 min, Bromide ion 9.0 min |

5. Dynamic moisture adsorption (DVS):
Dynamic moisture adsorption (DVS) curves were collected on DVS Intrinsic of Surface Measurement Systems (SMS). The relative humidity at 25° C. was corrected with the deliquescent points of LiCl, Mg (NO3) 2 and KCl. DVS test parameters are listed in Table 5.

TABLE 5

DVS test parameters

| Parameters | Settings |
|---|---|
| Temperature | 25° C. |
| Sample | 10-20 mg |
| Gas protection and flow speed | N2, 200 mL/min |
| dm/dt | 0.002%/min |
| Min dm/dt balance time | 10 min |
| Max balance time | 180 min |
| RH range | 0% RH-95% RH |
| RH gradient | 10%(0% RH-90% RH, 90% RH-0% RH) 5%(90% RH-95% RH, 95% RH-90% RH) |

Example 1: Preparation of Crystal Form B of Hydrochloride

At 20° C., 1 g OAD2 was added to 5 ml 2-methyltetrahydrofuran, and then 1.4 ml of 1 mol/L hydrochloric acid solution was dropwise added. The mixture was stirred for 2 hours. XRPD was used to monitor whether a new crystal form was formed. After the completion of transformation and crystallization, crystal form B of hydrochloride was obtained after suction filtration and drying at 50° C., with a salt acid to base formation molar ratio of 1:1.

Example 2: Preparation of Crystal Form C of Hydrochloride 0.3 g OAD2 was dissolved in an acetone/water solution containing hydrochloric acid (29.2 l), and the mixture was stirred at room temperature. XRPD was used to monitor whether the solid had transformed into crystals. After the completion of transformation, crystal form C of hydrochloride was obtained after centrifugation and dryness, with a salt acid to base formation molar ratio of 1:1.

Examples 3 to 12: Screening of Other Crystalline Salt Complexes and the Preparation Process Thereof According to the method of Example 1 or 2, other crystalline acid salts were prepared, and the specific results were shown in Table 6. The results showed that, not all acids whose ΔpKa met the requirements could form salt with the free base; moreover, when the acid and the free base were fed at a ratio of 1:1, they might not always form a 1:1 salt.

TABLE 6

Investigation of acid salts

| Example | Crystalline complex | Solvent | Acid | Reference method | Salt formation molar ratio (acid/base) |
|---|---|---|---|---|---|
| 3 | Crystal form C of P-toluenesulfonate | tetrahydrofuran | p-toluenesulfonic acid | Example 1 | 1:1 |
| 4 | Crystal form C of tartrate | dichloromethane | tartaric acid | Example 2 | 1:1 |
| 5 | Crystal form C of citrate | dichloromethane | citric acid | Example 2 | 1:1 |
| 6 | Crystal form C of glycollate | dichloromethane | glycollic acid | Example 2 | 0.3:1 |
| 7 | Crystal form C of methanesulfonate | 2-methyl-tetrahydrofuran | methanesulfonic acid | Example 2 | 0.5:1 |
| 8 | Crystal form C of hydrobromide | dichloromethane | hydrobromic acid | Example 2 | 1:1 |
| 9 | Crystal form D of hydrobromide | 2-methyl-tetrahydrofuran | hydrobromic acid | Example 2 | 1:1 |
| 10 | Crystal form C of sulfate | 95% acetone-water solution | sulfuric acid | Example 2 | 1:1 |
| 11 | / | dichloromethane or 95% acetone-water solution | phosphoric acid | Example 2 | No acid formed |
| 12 | / | dichloromethane or 95% acetone-water solution | fumaric acid | Example 2 | No acid formed |

Example 13: Experimental Characterization of Crystalline Salt Complexes

The solid crystal forms were characterized by means of XRPD, DSC/TGA, etc., and the experimental data was shown in Table 7.

TABLE 7

Characterization data of the crystal forms

| Crystalline salt | TGA weight loss (%, (temperature/° C.)) | DSC endothermic peak (°, peak temperature) | Molar ratio (acid/base) |
|---|---|---|---|
| Crystal form B of hydrochloride | 6.3 (150) | 116, 193 | 1.0 |
| Crystal form C of hydrochloride | 3.7 (180) | 120.4, 177.6 | 1.0 |
| Crystal form C of sulfate | 3.5 (150) | 191.2 | 1.0 |
| Crystal form C of tartrate | 1.0 (150) | 170.3 | 1.0 |
| Crystal form C of citrate | 1.3 (100) | 122.4, 176.2 | 1.0 |
| Crystal form C of glycollate | 7.7 (170) | 156.8, 173.8 | 0.3 |
| Crystal form C of p-toluenesulfonate | 3.5 (150) | 100.4, 167.7 | 1.0 |
| Crystal form C of methanesulfonate | 2.5 (170) | 108.0, 164.1, 224.7 | 0.5 |
| Crystal form C of hydrobromide | 2.6 (150) | 212.8 | 1.0 |
| Crystal form D of hydrobromide | 2.3 (150) | 183.3 | 1.0 |

Example 14: Study of the Properties of Crystalline Salt Complexes

The Crystalline salts were subject to tests to determine and compare the pH solubility, hygroscopicity, and solid stability thereof.

1) Assessment of pH Solubility

The solubility of crystal form B of hydrochloride, crystal form C of p-toluenesulfonate, crystal form C of sulfate, and crystal form C of hydrobromide under different pH conditions were determined and compared, and the results were shown in Table 8. All the crystalline salts had low solubility in buffers of pH 3.0 and 5.0. In a buffer of pH 1.0, crystal form C of p-toluenesulfonate had significantly higher solubility than other crystalline salts.

TABLE 8

Comparison of solubility of various crystalline salts under different pH conditions

| Crystalline salt | Solubility (mg/mL) | | | | |
|---|---|---|---|---|---|
| | pH 1.0 | pH 2.0 | pH 3.0 | pH 5.0 | pH 7.0 |
| Crystal form B of hydrochloride | 0.381 | 0.017 | 0.002 | 0.001 | 0.109 |
| Crystal form C of p-toluenesulfonate | 1.423 | 0.118 | 0.001 | 0.001 | 0.093 |
| Crystal form C of sulfate | 0.811 | 0.074 | 0.001 | 0.001 | 0.096 |
| Crystal form C of hydrobromide | 0.496 | 0.016 | 0.001 | 0.004 | 0.039 |

2) Study of Hygroscopicity

Five crystalline salts were subject to DVS test (25° C., 80% RH). The results demonstrated that all the samples showed no change of crystal form before and after the DVS test; except that the sulfate had hygroscopicity, all the remaining samples had slight hygroscopicity; but the hygroscopicity was significantly improved as compared with OAD2 dihydrochloride. The results were shown in Table 9.

TABLE 9

| Crystalline salt | Moisture adsorption rate (%) | Change of crystal form, yes/no |
|---|---|---|
| Crystal form B of hydrochloride | 0.8 | No |
| Crystal form C of p-toluenesulfonate | 0.6 | No |
| Crystal form C of sulfate | 3.2 | No |
| Crystal form C of hydrobromide | 1.4 | No |
| OAD2 dihydrochloride | 8.3 | / |

3) Assessment of Solid Stability

The stability of crystal form B of hydrochloride, crystal form C of sulfate, crystal form C of p-toluenesulfonate and compound I was compared. After placement under a 40° C./100% RH condition for 1 week, physical and chemical stability was assessed by means of XRPD and HPLC, respectively, and the results were shown in Table 10. The results demonstrated that all the samples showed no distinct decrease in purity and no change of crystal form, and had superior stability; and particularly, crystal form C of p-toluenesulfonate showed the best stability.

TABLE 10

Comparison of stability of various crystalline salts

| Crystalline salt | HPLC (area %) | | Change of crystal form, yes/no |
|---|---|---|---|
| | Initiation | 40° C./100% RH/7 d | |
| Crystal form B of hydrochloride | 98.37 | 98.18 | No |
| Crystal form C of sulfate | 98.85 | 98.78 | No |
| Crystal form C of p-toluenesulfonate | 98.85 | 98.87 | No |
| compound I | 98.91 | 97.51 | / |

The invention claimed is:

1. A crystalline form of a salt of (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl)propionic acid (OAD2), selected from the group consisting of the following:
  crystal form B of hydrochloride salt of OAD2 (form B),
  crystal form C of hydrochloride salt of OAD2 (form C),
  crystal form C of p-toluenesulfonate salt of OAD2 (form C),
  crystal form C of tartrate salt of OAD2 (form C),
  crystal form C of citrate salt of OAD2 (form C),
  crystal form C of glycollate salt of OAD2 (form C),
  crystal form C of methanesulfonate salt of OAD2 (form C),
  crystal form C of hydrobromide salt of OAD2 (form C),
  crystal form D of hydrobromide salt of OAD2 (form D), and
  crystal form C of sulfate salt of OAD2 (form C).

2. The crystalline form of claim 1, wherein the crystalline form is a crystalline form of the hydrochloride salt of OAD2 and is characterized as having an X-ray powder diffraction pattern comprising peaks at the following diffraction angles (2θ): 5.3±0.2°, 9.2±0.2°, 10.3±0.2°, 13.2±0.2°, and 14.8±0.2° as measured using Cu, Kα radiation (form B).

3. The crystalline form of claim 1, wherein the crystalline form is a crystalline form of the hydrochloride salt of OAD2 and is characterized as having an X-ray powder diffraction pattern comprising substantially the same peaks at the 2θ diffraction angles as shown in FIG. 1 (form B).

4. The crystalline form of claim 1, wherein the crystalline form is a crystalline form of the hydrochloride salt of OAD2 and is characterized as having an X-ray powder diffraction pattern comprising peaks at the following diffraction angles (2θ): 8.9±0.2°, 11.6±0.2°, 14.3±0.2°, 15.9±0.2°, 21.4±0.2°, and 23.1±0.2° as measured using Cu, Kα radiation (form C).

5. The crystalline form of claim 1, wherein the crystalline form is a crystalline form of the hydrochloride salt of OAD2 and is characterized as having an X-ray powder diffraction pattern comprising substantially the same peaks at the 2θ diffraction angles as shown in FIG. 2 (form C).

6. The crystalline form of claim 1, wherein the crystalline form is a crystalline form of the p-toluenesulfonate salt of OAD2 and is characterized as having an X-ray powder diffraction pattern comprising peaks at the following diffraction angles (2θ): 4.7±0.2°, 5.4±0.2°, 9.7±0.2°, 13.1±0.2°, 16.4±0.2°, and 18.2±0.2° as measured using Cu, Kα radiation (form C).

7. The crystalline form of claim 1, wherein the crystalline form is a crystalline form of the p-toluenesulfonate salt of OAD2 and is characterized as having an X-ray powder diffraction pattern comprising substantially the same peaks at the 2θ diffraction angles as shown in FIG. 3 (form C).

8. The crystalline form of claim 1, wherein the crystalline form is a crystalline form of the tartrate salt of OAD2 and is characterized as having an X-ray powder diffraction pattern comprising peaks at the following diffraction angles (2θ): 7.8±0.2°, 9.9±0.2°, 10.1±0.2°, and 15.6±0.2° as measured using Cu, Kα radiation (form C).

9. The crystalline form of claim 1, wherein the crystalline form is a crystalline form of the tartrate salt of OAD2 and is characterized as having an X-ray powder diffraction pattern comprises substantially the same peaks at the 2θ diffraction angles as shown in FIG. 4 (form C).

10. The crystalline form of claim 1, wherein the crystalline form is a crystalline form of the citrate salt of OAD2 and is characterized as having an X-ray powder diffraction pattern comprising peaks at the following diffraction angles (2θ): 4.5±0.2°, 6.5±0.2°, and 15.9±0.2° as measured using Cu, Kα radiation (form C).

11. The crystalline form of claim 1, wherein the crystalline form is a crystalline form of the p-toluenesulfonate salt of OAD2 and is characterized as having an X-ray powder diffraction pattern comprising substantially the same peaks at the 2θ diffraction angles as shown in FIG. 5 (form C).

12. The crystalline form of claim 1, wherein the crystalline form is a crystalline form of the glycollate salt of OAD2 and is characterized as having an X-ray powder diffraction pattern comprising peaks at the following diffraction angles (2θ): 6.0±0.2°, 12.1±0.2°, 13.6±0.2°, 18.2±0.2°, and 24.3±0.2° as measured using Cu, Kα radiation (form C).

13. The crystalline form of claim 1, wherein the crystalline form is a crystalline form of the glycollate salt of OAD2 and is characterized as having an X-ray powder diffraction pattern comprising substantially the same peaks at the 2θ diffraction angles as shown in FIG. 6 (form C).

14. The crystalline form of claim 1, wherein the crystalline form is a crystalline form of the methanesulfonate salt of OAD2 and is characterized as having an X-ray powder diffraction pattern comprising peaks at the following diffraction angles (2θ): 10.2±0.2°, 12.8±0.2°, 13.8±0.2°, 14.4±0.2°, and 22.2±0.2° as measured using Cu, Kα radiation (form C).

15. The crystalline form of claim 1, wherein the crystalline form is a crystalline form of the methanesulfonate salt of OAD2 and is characterized as having an X-ray powder diffraction pattern comprising substantially the same peaks at the 2θ diffraction angles as shown in FIG. 7 (form C).

16. The crystalline form of claim 1, wherein the crystalline form is a crystalline form of the hydrobromide salt of OAD2 and is characterized as having an X-ray powder diffraction pattern comprising peaks at the following diffraction angles (2θ): 4.6±0.2°, 15.7±0.2°, and 23.7±0.2° as measured using Cu, Kα radiation (form C).

17. The crystalline form of claim 1, wherein the crystalline form is a crystalline form of the hydrobromide salt of OAD2 and is characterized as having an X-ray powder diffraction pattern comprising substantially the same peaks at the 2θ diffraction angles as shown in FIG. 8 (form C).

18. The crystalline form of claim 1, wherein the crystalline form is a crystalline form of the hydrobromide salt of OAD2 and is characterized as having an X-ray powder diffraction pattern comprising peaks at the following diffraction angles (2θ): 4.7±0.2°, 8.8±0.2°, 15.9±0.2°, and 17.8±0.2° (form D).

19. The crystalline form of claim 1, wherein the crystalline form is a crystalline form of the hydrobromide salt of OAD2 and is characterized as having an X-ray powder diffraction pattern comprising substantially the same peaks at the 2θ diffraction angles as shown in FIG. 9 (form D).

20. The crystalline form of claim 1, wherein the crystalline form is a crystalline form of the sulfate salt of OAD2 and is characterized as having an X-ray powder diffraction pattern comprising peaks at the following diffraction angles (2θ): 3.4±0.2°, 8.7±0.2°, and 15.2±0.2° as measured using Cu, Kα radiation (form C).

21. The crystalline form of claim 1, wherein the crystalline form is a crystalline form of the sulfate salt of OAD2 and is characterized as having an X-ray powder diffraction pattern comprising substantially the same peaks at the 2θ diffraction angles as shown in FIG. 10 (form C).

22. A pharmaceutical composition comprising the crystalline salt form of (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl)propionic acid (OAD2) of claim 1, and a pharmaceutically acceptable carrier.

23. A method of treating diabetes in a patient in need thereof, the method comprising administering to the patient the crystalline salt form of (S)-2-(3S,8S)-3-(4-(3,4-dichlorobenzyloxy)phenyl-7-((S)-1-phenylpropyl)-2,3,6,7,8,9-hexahydro-[1,4]-dioxino[2,3-g]isoquinolin-8-ylformylamino)-3-(4-(2,3-dimethylpyridin-4-yl)phenyl)propionic acid (OAD2) of claim 1.

* * * * *